United States Patent
Dehe et al.

(10) Patent No.: US 10,495,612 B2
(45) Date of Patent: *Dec. 3, 2019

(54) PHOTOACOUSTIC GAS SENSOR DEVICE AND A METHOD FOR ANALYZING GAS

(71) Applicant: Infineon Technologies AG, Neubiberg (DE)

(72) Inventors: Alfons Dehe, Reudlingen (DE); Stefan Kolb, Unterschleissheim (DE); Horst Theuss, Wenzenbach (DE)

(73) Assignee: Infineon Technologies AG, Neubiberg (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/341,567

(22) Filed: Nov. 2, 2016

(65) Prior Publication Data
US 2017/0074834 A1  Mar. 16, 2017

Related U.S. Application Data

(63) Continuation of application No. 14/052,959, filed on Oct. 14, 2013, now Pat. No. 9,513,261.

(51) Int. Cl.
*G01N 29/24* (2006.01)
*G01N 21/17* (2006.01)
*G01N 29/30* (2006.01)

(52) U.S. Cl.
CPC ..... *G01N 29/2425* (2013.01); *G01N 21/1702* (2013.01); *G01N 29/2418* (2013.01);
(Continued)

(58) Field of Classification Search
CPC ....... G01N 21/1702; G01N 2021/1704; G01N 29/242; G01N 29/2418; G01N 21/37; G01L 9/0079; H04R 23/008; G01J 5/42
See application file for complete search history.

(56) References Cited

U.S. PATENT DOCUMENTS

| | | |
|---|---|---|
| 4,253,770 A | 3/1981 | Horiba |
| 4,436,428 A | 3/1984 | Watanabe et al. |

(Continued)

FOREIGN PATENT DOCUMENTS

| | | |
|---|---|---|
| CN | 1950693 A | 4/2007 |
| CN | 101095042 A | 12/2007 |

(Continued)

OTHER PUBLICATIONS

Kuusela, T., et al. "Photoacoustic gas detection using a cantilever microphone and III-V mid-IR LEDs." Vibrational spectroscopy 51.2 (2009): 289-293.*

(Continued)

*Primary Examiner* — Harshad R Patel
(74) *Attorney, Agent, or Firm* — Schiff Hardin LLP

(57) ABSTRACT

A photoacoustic gas sensor device for analyzing gas includes an emitter module and a pressure-sensitive module. The emitter module is arranged on a carrier substrate and emits light pulses. The pressure-sensitive module is arranged on the carrier substrate within a reference gas volume. The reference gas volume is separated from a volume intended to be filled with a gas to be analyzed. Further, the pressure-sensitive module generates a sensor signal indicating information on an acoustic wave caused by light pulses emitted by the emitter module interacting with a reference gas within the reference gas volume. Additionally, the emitter module is arranged so that light pulses emitted by the emitter module reach the reference gas volume after crossing the volume intended to be filled with the gas to be analyzed.

17 Claims, 23 Drawing Sheets

(52) U.S. Cl.
CPC ..... *G01N 29/30* (2013.01); *G01N 2021/1704* (2013.01); *G01N 2291/021* (2013.01)

(56) References Cited

U.S. PATENT DOCUMENTS

| | | | |
|---|---|---|---|
| 5,616,826 A | | 4/1997 | Pellaux et al. |
| 5,869,749 A | * | 2/1999 | Bonne .................... G01N 21/03 250/339.12 |
| 5,933,245 A | * | 8/1999 | Wood ................. G01N 21/1702 356/246 |
| 6,006,585 A | * | 12/1999 | Forster ............... G01N 21/1702 250/343 |
| 6,082,178 A | * | 7/2000 | Bernstein ........... G01N 21/1702 73/24.02 |
| 6,222,190 B1 | * | 4/2001 | Bernstein .................. G01J 5/42 250/343 |
| 6,344,647 B1 | * | 2/2002 | Jourdain ............ G01N 21/1702 250/339.07 |
| 7,164,479 B2 | * | 1/2007 | Johansen ............... G01L 9/0079 356/506 |
| 7,208,737 B2 | | 4/2007 | Kauppinen |
| 8,847,197 B2 | * | 9/2014 | Pickett .................. C09K 11/025 257/13 |
| 8,953,165 B2 | | 2/2015 | Feitisch et al. |
| 9,829,428 B2 | * | 11/2017 | Yang .................. G01N 21/1702 |
| 2003/0208133 A1 | * | 11/2003 | Mault ................... A61B 5/0002 600/532 |
| 2007/0151325 A1 | | 7/2007 | Kauppinen |
| 2008/0137886 A1 | * | 6/2008 | Schrank ................ H04R 19/04 381/174 |
| 2008/0277586 A1 | * | 11/2008 | Cardinale ................. G01J 5/02 250/339.13 |
| 2011/0290002 A1 | * | 12/2011 | Heidrich ............ G01N 21/1702 73/24.02 |
| 2011/0296900 A1 | * | 12/2011 | Thorson ............. G01N 21/1702 73/24.02 |
| 2012/0260719 A1 | * | 10/2012 | Schade ............. G01N 21/1702 73/24.02 |
| 2012/0266655 A1 | * | 10/2012 | Brun .................. G01N 21/1702 73/24.02 |
| 2012/0267532 A1 | * | 10/2012 | Udrea .................... H05B 3/267 250/338.5 |
| 2012/0318041 A1 | * | 12/2012 | Youngner .......... G01N 21/1702 73/24.02 |
| 2015/0101395 A1 | * | 4/2015 | Dehe ................. G01N 29/2418 73/24.02 |
| 2016/0282259 A1 | * | 9/2016 | Kolb .................. G01N 29/022 |
| 2017/0067859 A1 | * | 3/2017 | Kolb ...................... G01N 29/30 |
| 2017/0212036 A1 | * | 7/2017 | Mueller ............. G01N 21/1702 |

FOREIGN PATENT DOCUMENTS

| | | | | |
|---|---|---|---|---|
| CN | 101303298 A | | 11/2008 | |
| KR | 20110132982 A | * | 12/2011 | ......... G01N 21/1702 |
| WO | WO 9915879 A1 | * | 4/1999 | ......... G01N 21/1702 |
| WO | WO-2006/007446 A2 | | 1/2006 | |

OTHER PUBLICATIONS

Ohlckers, Per, et al. "A photoacoustic gas sensing silicon microsystem." Transducers' 01 Eurosensors XV. Springer, Berlin, Heidelberg, 2001. 780-783.*

Schulz, O., Legner, W., Müller, G., Schjølberg-Henriksen, K., Ferber, A., Moe, S., . . . & Suphan, K. H. (2007). Photoacoustic gas sensing microsystems. Proc. AMA.*

Fonsen, J., et al. "Dual cantilever enhanced photoacoustic detector with pulsed broadband IR-source." Vibrational Spectroscopy 50.2 (2009): 214-217.*

Keränen, Kimmo, et al. "Portable methane sensor demonstrator based on LTCC differential photo acoustic cell and silicon cantilever." Procedia Engineering 47 (2012): 1438-1441.*

Ledermann, Nicolas, et al. "Piezoelectric Pb (Zrx, Ti1-x) O3 thin film cantilever and bridge acoustic sensors for miniaturized photoacoustic gas detectors." Journal of Micromechanics and Microengineering 14.12 (2004): 1650.*

Kauppinen, Jyrki, et al. "High sensitivity in gas analysis with photoacoustic detection." Microchemical journal 76.1-2 (2004): 151-159.*

San, et al., "A Silicon Micromachined Infrared Emitter Based on SOI Wafer", vol. 6836, 2008, 8 pages.

Dong, et al., "Compact Portable QEPAS Multi-Gas Sensor", vol. 7945, © 2011, 8 pages.

Florescu, et al., "Improving Solar Cell Efficiency Using Photonic Band-Gap Materials", www.sciencedirect.com, vol. 91, pp. 1599-1610, © 2007.

Elia, et al., "Photoacoustic Techniques for Trace Gas Sensing Based on Semiconductor Laser Sources", vol. 9, pp. 9616-9628, 2009, www.mdpi.com/journal/sensors.

Firebaugh, et al., "Miniaturization and Integration of Photoacoustic Detection with a Microfabricated Chemical Reactor System", Journal of Microelectromechanical Systems, vol. 10, No. 2, Jun. 2001, pp. 232-237.

Harren, et al., "Photoacoustic Spectroscopy in Trace Gas Monitoring", Encyclopedia of Analytical Chemistry, pp. 2203-2226, © 2000.

Konz, et al., "Micromachine IR-Source With Excellent Blackbody Like Behaviour", vol. 5836, pp. 540-548, © 2005.

Office Action dated Nov. 1, 2016 for Chinese Patent Application No. 201410539398.6.

Office Action dated Jul. 3, 2017 for Chinese Patent Application No. 201410539398.6.

* cited by examiner

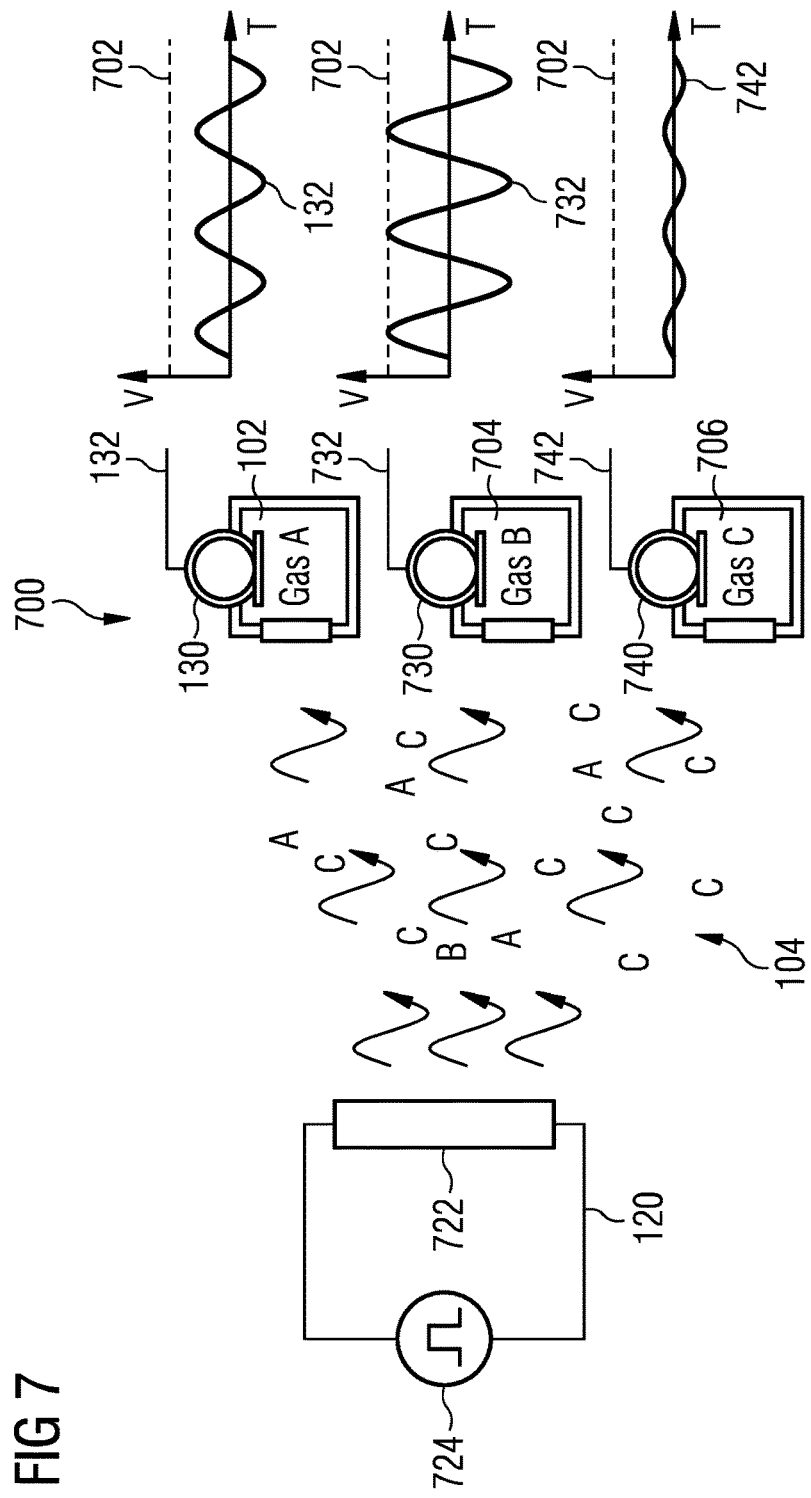

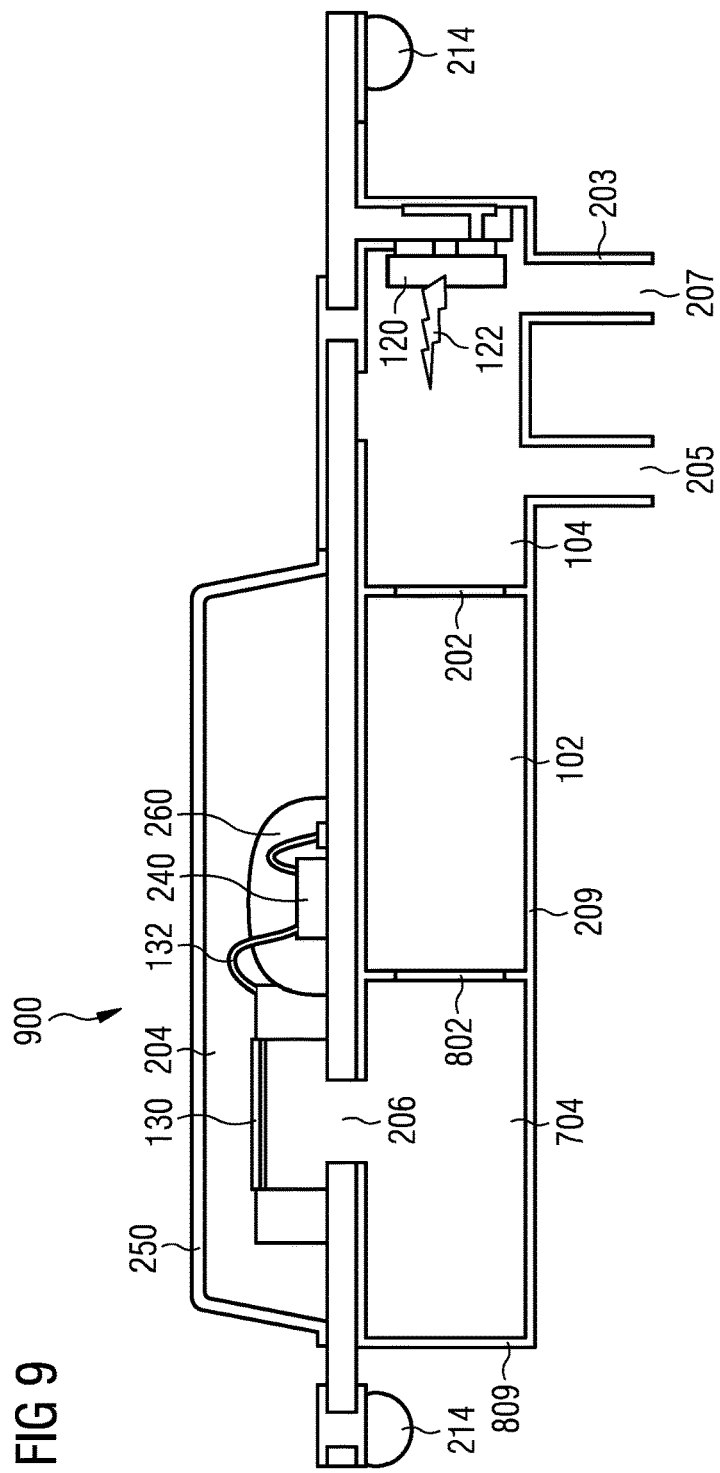

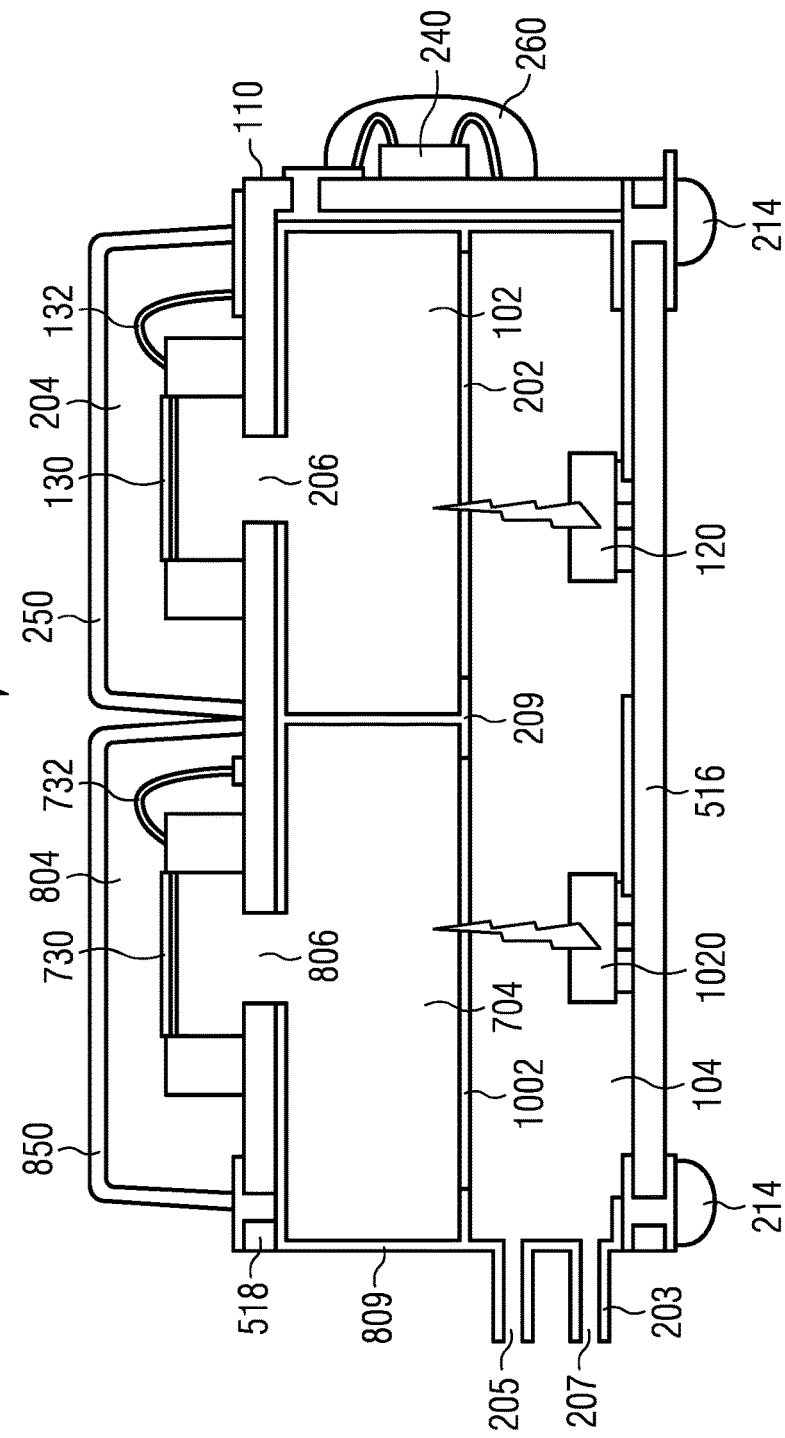

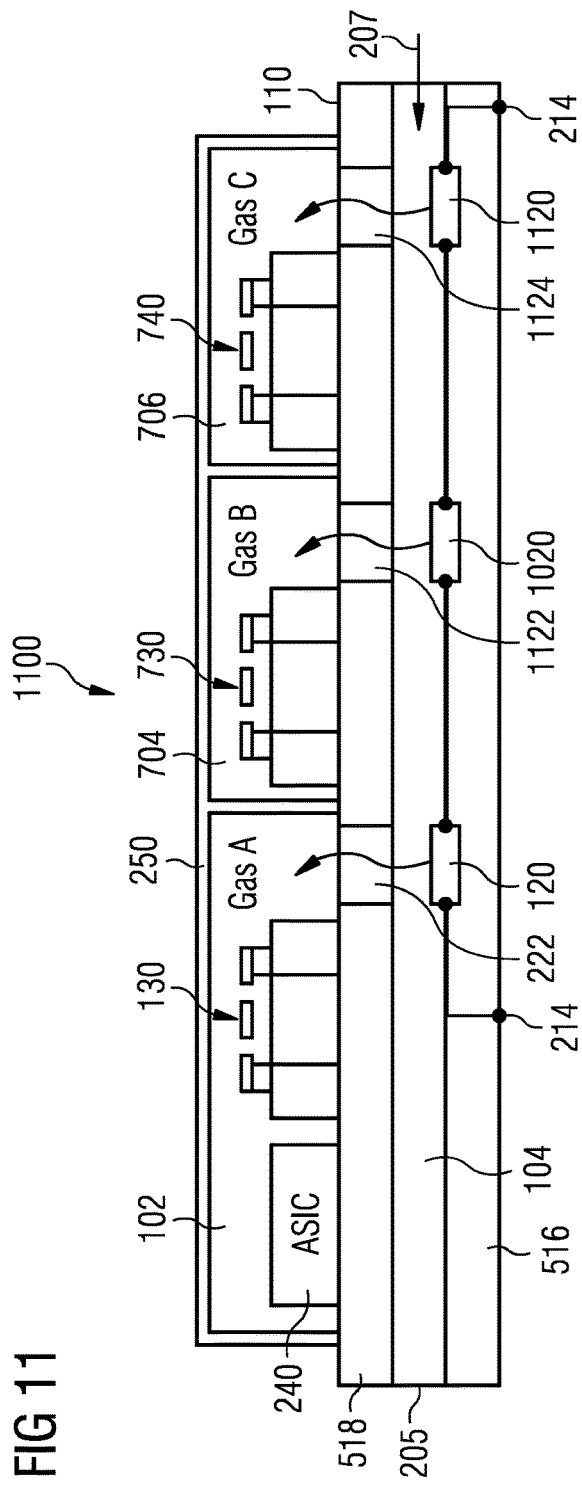

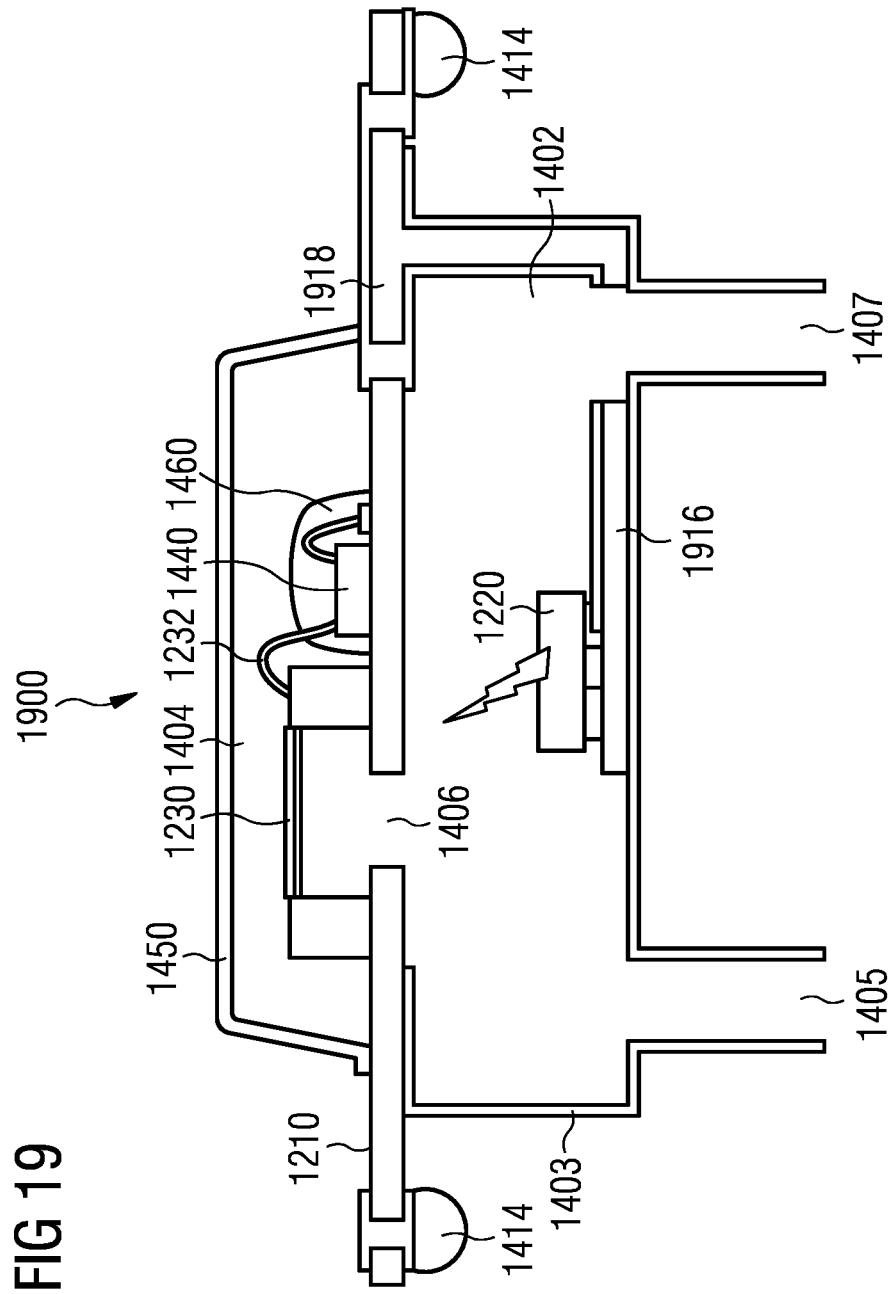

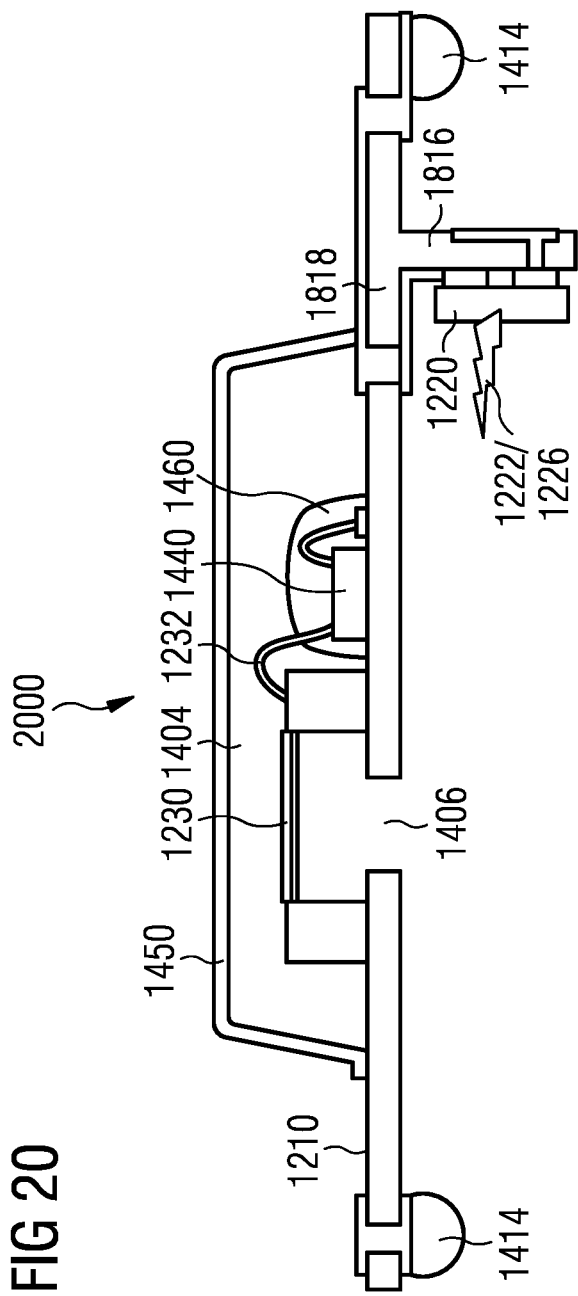

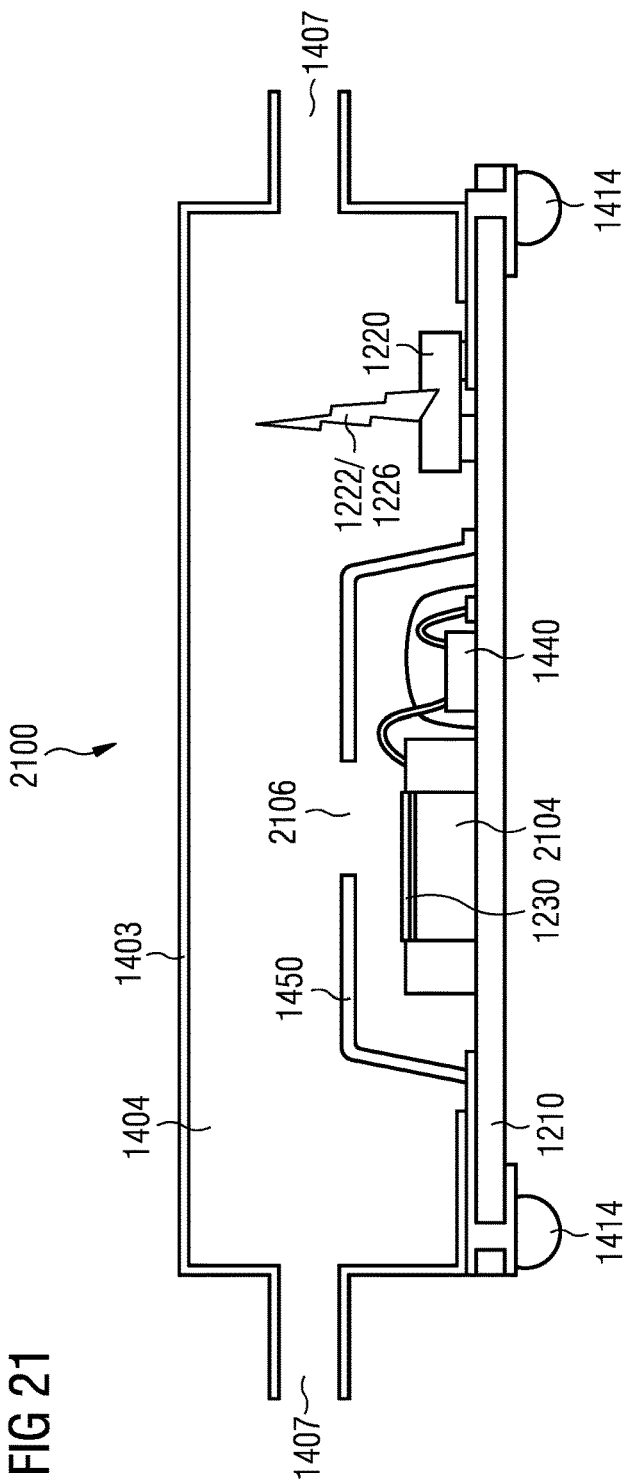

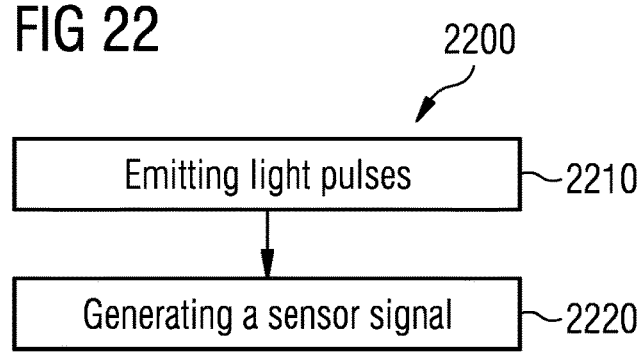
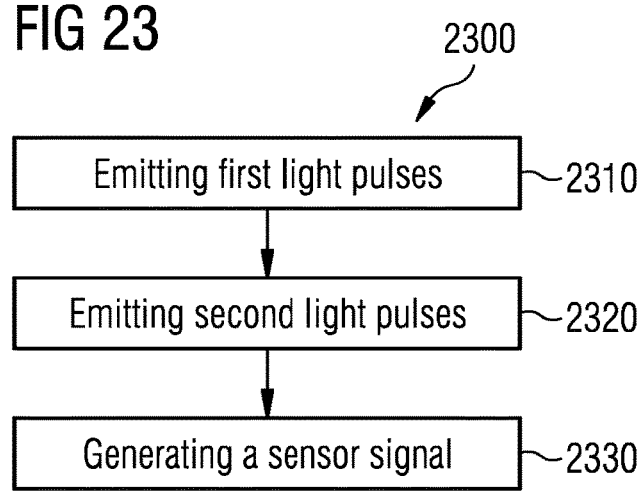

PHOTOACOUSTIC GAS SENSOR DEVICE AND A METHOD FOR ANALYZING GAS

TECHNICAL FIELD

Embodiments relate to photoacoustic measurement concepts and in particular to a photoacoustic gas sensor device and a method for analyzing gas.

BACKGROUND

The photoacoustic effect relates to the formation of sound waves, following light absorption in a medium. In order to obtain this effect, the light intensity is varied. The photoacoustic effect can be quantified by measuring the formed sound (e.g. pressure changes) with appropriate detectors. The time variation of the electric output from these detectors can be called photoacoustic signal. These measurements can be used to determine certain properties of the studied medium. For example, the composition of gas can be analyzed. It is desired to implement a photoacoustic gas sensor concept providing high accuracy with low effort.

SUMMARY

An embodiment relates to a photoacoustic gas sensor device for analyzing gas comprising an emitter module and a pressure sensitive module. The emitter module is arranged on a carrier substrate and is configured to emit light pulses. The pressure-sensitive module is arranged on the carrier substrate within a reference gas volume. The reference gas volume is separated from a volume intended to be filled with a gas to be analyzed. Further, the pressure-sensitive module is configured to generate a sensor signal indicating information on an acoustic wave caused by light pulses emitted by the emitter module interacting with a reference gas within the reference gas volume. The emitter module is arranged so that light pulses emitted by the emitter module reach the reference gas volume after crossing the volume intended to be filled with the gas to be analyzed.

Due to the placement of the emitter module so that the light pulses provided by the emitter module pass the volume intended to be filled with the gas to be analyzed before entering the reference gas volume, only the not absorbed portion of the light pulses reaches the reference gas volume and causes an acoustic wave. By implementing the emitter module and the pressure-sensitive module on a common carrier substrate in combination with a placement of the pressure-sensitive module within a reference gas volume, a gas can be analyzed with regard to one or more components contained by the reference gas with high accuracy and low effort.

Some embodiments relate to a photoacoustic gas sensor device for analyzing gas comprising an emitter module and a pressure-sensitive module. The emitter module is arranged on a carrier substrate and is configured to emit first light pulses within a first frequency range and with a first temporal occurrence characteristic and second light pulses within a second frequency range and with a second temporal occurrence characteristic. The pressure-sensitive module is arranged on the carrier substrate and is configured to generate a sensor signal indicating information on first acoustic waves caused by the first light pulses emitted by the emitter module interacting with a gas to be analyzed and second acoustic waves caused by the second light pulses emitted by the emitter module interacting with the gas to be analyzed.

By implementing an emitter module capable of emitting light pulses within a first frequency range and light pulses within a second frequency range, different components of a gas can be activated or excited in order to cause acoustic waves. The acoustic waves caused by the different light pulses can be differentiated by the pressure-sensitive module due to the different temporal occurrence characteristic of the first light pulses and the second light pulses. By implementing the emitter module and the pressure sensitive module on a common carrier substrate, various components of a gas can be analyzed simultaneously with low effort.

BRIEF DESCRIPTION OF THE FIGURES

Some embodiments of apparatuses and/or methods will be described in the following by way of example only, and with reference to the accompanying figures, in which

FIG. 7 shows a schematic illustration of a photoacoustic gas sensor device;

FIGS. 8A to 11 show schematic cross-sections of photoacoustic gas sensor devices;

FIGS. 14 to 21 show schematic cross-sections of photoacoustic gas sensor devices;

FIG. 22 shows a flowchart of a method for analyzing gas; and

FIG. 23 shows a flowchart of a method for analyzing gas.

DETAILED DESCRIPTION

Various example embodiments will now be described more fully with reference to the accompanying drawings in which some example embodiments are illustrated. In the figures, the thicknesses of lines, layers and/or regions may be exaggerated for clarity.

Accordingly, while example embodiments are capable of various modifications and alternative forms, embodiments thereof are shown by way of example in the figures and will herein be described in detail. It should be understood, however, that there is no intent to limit example embodiments to the particular forms disclosed, but on the contrary, example embodiments are to cover all modifications, equivalents, and alternatives falling within the scope of the disclosure. Like numbers refer to like or similar elements throughout the description of the figures.

It will be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present. Other words used to describe the relationship between elements should be interpreted in a like fashion (e.g., "between" versus "directly between," "adjacent" versus "directly adjacent," etc.).

The terminology used herein is for the purpose of describing particular embodiments only and is not intended to be limiting of example embodiments. As used herein, the singular forms "a," "an" and "the" are intended to include the plural forms as well, unless the context clearly indicates otherwise. It will be further understood that the terms "comprises," "comprising," "includes" and/or "including," when used herein, specify the presence of stated features, integers, steps, operations, elements and/or components, but do not preclude the presence or addition of one or more other features, integers, steps, operations, elements, components and/or groups thereof.

Unless otherwise defined, all terms (including technical and scientific terms) used herein have the same meaning as commonly understood by one of ordinary skill in the art to which example embodiments belong. It will be further understood that terms, e.g., those defined in commonly used dictionaries, should be interpreted as having a meaning that is consistent with their meaning in the context of the relevant art and will not be interpreted in an idealized or overly formal sense unless expressly so defined herein.

Figure 1:
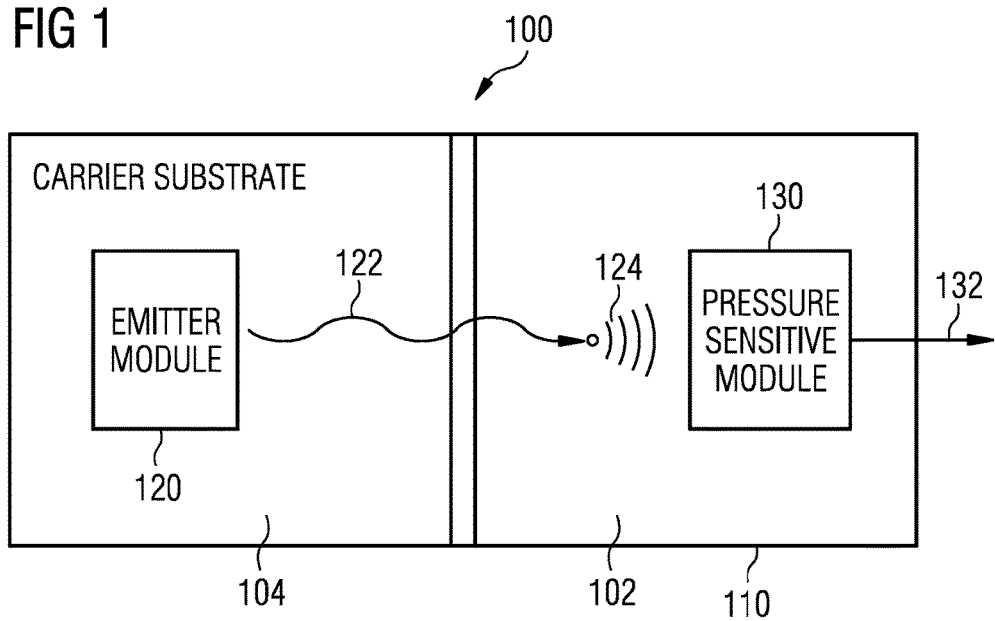
FIG. 1 shows a schematic illustration of a photoacoustic gas sensor device.

FIG. 1 shows a schematic illustration of a photoacoustic gas sensor device 100 for analyzing gas according to an embodiment. The photoacoustic gas sensor device 100 comprises an emitter module 120 and a pressure-sensitive module 130 arranged on a common carrier substrate 110. The emitter module 120 is able to or configured to emit light pulses 122. The pressure-sensitive module 130 is arranged within a reference gas volume 102. The reference gas volume 102 is separated from a volume 104 intended to be filled with a gas to be analyzed. The pressure-sensitive module 130 generates a sensor signal 132 indicating information on an acoustic wave 124 caused by light pulses 122 emitted by the emitter module 120 interacting with a reference gas within the reference gas volume 102. Further, the emitter module 120 is arranged so that light pulses 122 emitted by the emitter module 120 reach the reference gas volume 102 after crossing the volume 104 intended to be filled with the gas to be analyzed.

Due to the placement of the emitter module so that the light pulses provided by the emitter module pass the volume intended to be filled with the gas to be analyzed before entering the reference gas volume, only the not absorbed portion of the light pulses reaches the reference gas volume and causes an acoustic wave. By implementing the emitter module and the pressure-sensitive module on a common carrier substrate in combination with a placement of the pressure-sensitive module within a reference gas volume, a gas can be analyzed with regard to one or more components contained by the reference gas with high accuracy and low effort.

The photoacoustic gas sensor device 100 is a device capable of analyzing gas based on the photoacoustic effect. For this, the photoacoustic gas sensor device 100 comprises an emitter module 120 for generating light pulses to be absorbed by a gas in order to cause an acoustic wave and a pressure-sensitive module 130 for detecting the acoustic wave and generating a corresponding sensor signal 132.

The emitter module 120 and the pressure-sensitive module 130 are arranged on a common carrier substrate 110. In this connection, the carrier substrate 110 may be a semiconductor die comprising an emitter circuitry or emitter structure representing the emitter module 120 and a pressure-sensitive circuitry or pressure-sensitive structure representing the pressure sensitive module 130, for example. In this example, the separation of the reference gas volume 102 with the pressure-sensitive module 130 can be implemented by an appropriate package encapsulating the portion of the carrier substrate 110 comprising the pressure-sensitive module 130.

Alternatively, the carrier substrate 110 may be a structured substrate (e.g. organic like a printed circuit board PCB, a metal grid like a lead frame or a flex board) providing a surface for mounting the emitter module 120 implemented by a surface-mounted device SMD (e.g. semiconductor die) and the pressure-sensitive module 130 implemented on another or the same surface-mounted device, for example. In this example, the pressure-sensitive module 130 (e.g. semiconductor die) can be enclosed within a reference gas volume 102 by an appropriate package (e.g. cap or lid together with the carrier substrate enclosing the pressure-sensitive module). In other words, the carrier substrate 110 may be a printed circuit board representing a rigid substrate or a flex substrate or a combination between flex and rigid substrate, for example.

In other words, the emitter module 120 and the pressure-sensitive module 130 may be implemented on the same semiconductor die representing the carrier substrate 110 or the pressure-sensitive module 130 and the emitter module 120 are implemented on different semiconductor dies mounted on a common carrier substrate 110, for example.

The emitter module 120 is configured to emit light pulses 122. These light pulses 122 may comprise frequency portions in a large frequency range or frequency portions in only one or more narrow frequency bands.

For example, the light pulses generated by the emitter module 120 may comprise frequency portions within the infrared frequency region (e.g. 780 nm to 1 mm or between 300 GHz and 400 THz) or visible frequency region. Alternatively, the emitter module may emit light pulses within a narrow frequency band adjusted to the gas to be analyzed or a component of the gas to be analyzed (e.g. for selectively exciting an absorption within the gas to be analyzed).

Further, the emitter module 120 can generate the light pulses with a predefined temporal characteristic. For example, the light pulses can be obtained by varying the light intensity of the emitted light (e.g. by modulating the light or by generating single flashes of light). For example, the emitter module 120 may be triggered periodically causing light pulses with predefined time intervals in between or with a predefined temporal frequency.

The emitter module 120 may be implemented in various ways. For example, the emitter module 120 may comprise a thermal emitter element, a photodiode element or a laser diode (e.g. infrared diode or infrared laser diode).

The pressure-sensitive module 130 is configured to generate a signal indicating information on a pressure or pressure variation applied to the pressure-sensitive module 130, for example. For example, the pressure-sensitive module 130 may comprise a membrane (e.g. of a microphone structure) or a piezoelectric element. The pressure applied to the membrane or the piezoelectric element (e.g. caused by reference gas within the reference gas volume) may cause a signal with a voltage or a current proportional to the applied pressure, a pressure variation or a pressure difference of time, for example. If a light pulse or a portion of a light pulse emitted by the emitter module 120 is absorbed by the reference gas or a component of the reference gas within the reference gas volume 102, an acoustic wave 124 is excited or generated. This acoustic wave 124 propagates through the reference gas volume 102 and reaches the pressure-sensitive module 130. This acoustic wave 124 causes a pressure variation at the pressure-sensitive module 130 so that the pressure-sensitive module 130 can generate the sensor signal 132 indicating information on the acoustic wave 124. This information may be a voltage or a current proportional to the pressure or a pressure variation caused by the acoustic wave 124, for example. The strength of the acoustic wave 124 may be proportional to the amount of light absorbed by the reference gas. Therefore, if a large amount or portion of the light pulses is already absorbed by the gas to be analyzed within the volume 104 intended to be filled with the gas to be analyzed, only a low portion of the light pulses (i.e. light pulses with low intensity) reaches the reference gas volume 102 causing a weak acoustic wave 124 and vice-versa. Consequently, the information contained by the sensor signal 132 can be used for determining portions of components within the gas to be analyzed.

The reference gas volume 102 is separated from the volume 104 intended to be filled with the gas to be analyzed. In other words, the reference gas volume 102 may be an encapsulated volume, which can be filled with a reference gas. For example, a reference gas volume 102 can be formed by encapsulating the pressure-sensitive module 130 between the carrier substrate 110 and a cap, housing or lid, for example. Also other implementations may be possible as long as a reference gas at least partly surrounding the pressure-sensitive module 130 can be separated from a gas to be analyzed within the volume 104 intended to be filled with the gas to be analyzed.

The volume 104 intended to be filled with the gas to be analyzed can be an open volume (e.g. free access to the photoacoustic gas sensor device for gas in the proximity of the photoacoustic gas sensor device) or may be an encapsulated volume with a gas inlet and a gas outlet, for example.

The emitter module 120 may be arranged within the volume 104 intended to be filled with the gas to be analyzed as indicated in FIG. 1. Alternatively, the emitter module 120 may be separated from the reference gas volume 102 and the volume 104 intended to be filled with the gas to be analyzed (e.g. FIG. 2) or may be arranged within the reference gas volume 102 (e.g. FIG. 6). In the latter case, the emitter module 120 may emit the light pulses from the reference gas volume 102 into the volume 104 intended to be filled with the gas to be analyzed and a non-absorbed portion may again reach the reference gas volume 102 so that the light pulses reach the reference gas volume 102 also after crossing the volume 104 intended to be filled with the gas to be analyzed, for example. Alternatively, the emitter module 120 may be arranged so that light emitted by the emitter module reaches the reference gas volume 102 after only crossing the volume 104 intended to be filled with the gas to be analyzed without crossing another volume filled with gas (e.g. if the emitter module is arranged within the volume intended to be filled with the gas to be analyzed or arranged separated from the reference gas volume and the volume intended to be filled with the gas to be analyzed). In this way, only the portion of the light pulses not already absorbed by the gas to be analyzed can reach the reference gas volume 102 so that variations of the absorptions within the gas to be analyzed have a large influence resulting in a high accuracy of the gas analysis.

As already mentioned, the pressure-sensitive module 130 may comprise optionally at least a membrane. This membrane may be moved by an acoustic wave 124 caused by light pulses 122 emitted by the emitter module 120 interacting with a reference gas within the reference gas volume 102. The membrane can be arranged so that the reference gas within the reference gas volume 102 surrounds the membrane during analyzing gas. In other words, during operation of the photoacoustic gas sensor device 100 a reference gas is located within the reference gas volume 102, which may be present at both sides of the membrane (e.g. the volume at the front side and the back side of the membrane may be connected by venting holes through the membrane), for example. Alternatively, the pressure-sensitive module 130 may comprise a cavity at one side of the membrane separated from the reference gas volume.

Optionally, the emitter module 120 and the pressure-sensitive module 130 can be arranged so that at least a volume located at one side (e.g. backside) of the membrane cannot be reached by light pulses emitted by the emitter module 120 or so that less than 1% (or less than 10%, less than 5% or less than 0.1%) of the light pulses or portions of the light pulses emitted by the emitter module 120 is able to reach the volume located at the one side (e.g. backside) of the membrane. In other words, the emitter module 120 and/or the pressure-sensitive module 130, the carrier substrate 110 and/or a part of the package of the photoacoustic gas sensor device 100 may provide the possibility of avoiding light emitted by the emitter module 120 reaching a backside of the membrane of the pressure-sensitive module 130, for example. In this way, an acoustic wave can be only caused at one side of the membrane (e.g. at the front side of the membrane) so that a destructive interference with acoustic waves caused at the other side of the membrane can be avoided resulting in a large pressure variation at the membrane caused by absorbed light pulses.

Additionally, alternatively or optionally to one or more aspects mentioned above, the photoacoustic gas sensor device 100 may comprise an analyzing module configured to determine information on the gas to be analyzed based on the sensor signal 132. The analyzing module may comprise an electric circuit implemented together with the pressure-sensitive module 130 on the same semiconductor die. Alternatively, the analyzing module may be arranged on the carrier substrate 110 and implemented on a different semiconductor die than the pressure-sensitive module 130. In this way, the manufacturing processes and/or technologies may be better adapted to the requirements of the pressure-sensitive module 130 and the analyzing module respectively. For example, the analyzing module may be implemented in an easily scalable CMOS-technology (Complementary Metal Oxide Semiconductor), while the pressure-sensitive module may be implemented by an MEMS technology (Micro Electro Mechanical System) suitable for manufacturing movable parts (e.g. a membrane).

Alternatively to an emitter module with a single emitter element, emitting light pulses with a broadband frequency spectrum, the emitter module may emit light pulses with different narrowband frequency ranges and different temporal occurrence characteristics. In other words, the emitter module may emit first light pulses within a first frequency range and with a first temporal occurrence characteristic and second light pulses within a second frequency range and with a second temporal occurrence characteristic. The pressure-sensitive module 130 may generate a sensor signal 132 indicating information on first acoustic waves caused by the first light pulses emitted by the emitter module 120 interacting with a gas to be analyzed and second acoustic waves caused by the second light pulses emitted by the emitter module 120 interacting with the gas to be analyzed. In this way, several components of the gas to be analyzed can be analyzed simultaneously, for example.

Figure 2:
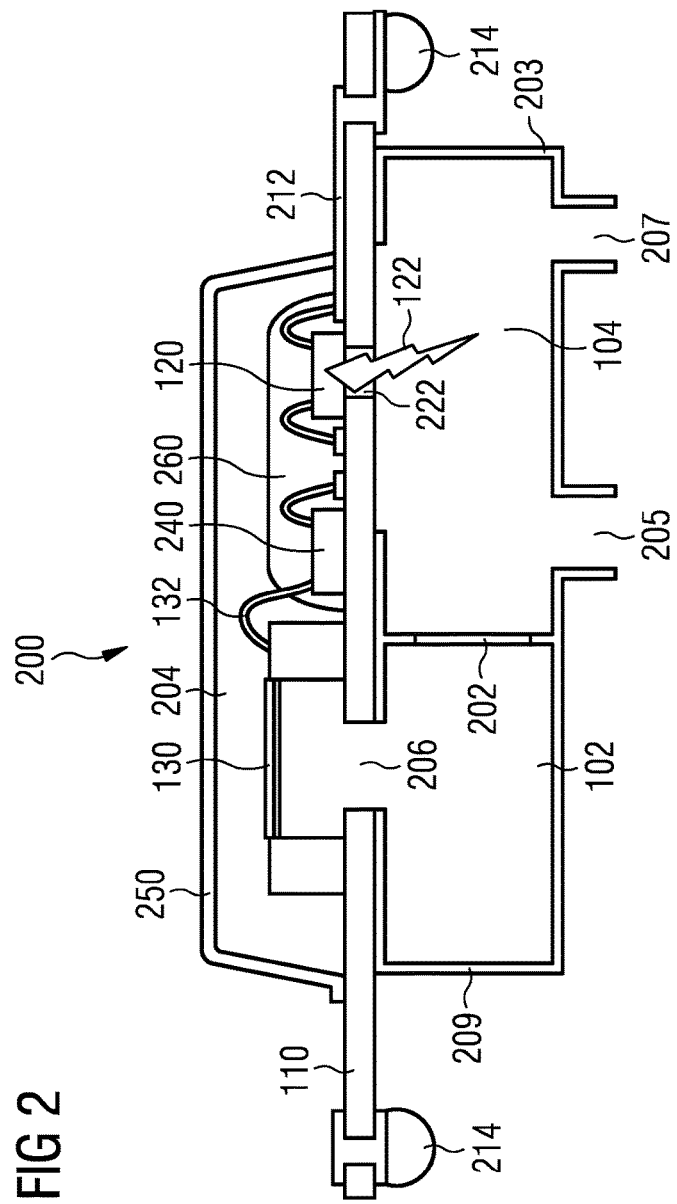
FIGS. 2 to 6 show schematic cross-sections of photoacoustic gas sensor devices.

FIG. 2 shows a schematic cross-section of a photoacoustic gas sensor device 200 according to an embodiment. The implementation of the photoacoustic gas sensor device 200 is similar to the implementation shown in FIG. 1. An emitter module 120, a pressure-sensitive module 130 and an analyzing module 240 are arranged on the same side of a carrier substrate 110.

The carrier substrate 110 is for example a structured substrate (e.g. organic printed circuit board, a metal grid or lead frame).

The emitter module 120 is an infrared IR emitter (e.g. IR-diode or laser diode) and can be assembled as chip (as shown in FIG. 2) or as complete packaged component, for example.

The analyzing module 240 may be implemented as a logic die (comprising logical electrical circuits) for signal conditioning or determining information on the gas to be analyzed based on the sensor signal 132 provided by the pressure-sensitive module 130, for example. The analyzing module 240 can be implemented by an application-specific integrated circuit (ASIC), for example.

The carrier substrate 110 comprises a basically flat geometry (e.g. neglecting topology or unevenness due to metal layers used for electrically conducting the different components). The pressure-sensitive module 130 may comprise a membrane on an MEMS die (Micro Electro Mechanical System semiconductor die). The emitter module 120 may be arranged above a hole or window through the carrier substrate 110 in order to emit light pulses 122 to the opposite side of the carrier substrate 110. For example, the hole or window may be an infrared (IR) window implemented by a hole or material with low infrared absorption (e.g. silicon), but can as well be a hole, if the emitter module 120 (IR chip) assembly may ensure an acoustically sealed back volume, for example.

The metal pads on the chips (the infrared emitter and the analyzing module) may be optionally protected by a casting compound 260 (e.g. epoxy), if exposed corrosive metal is involved (e.g. aluminum) for example.

The analyzing module 240 is laterally arranged between the pressure-sensitive module 130 and the emitter module 120 on the same side of the carrier substrate 110. The pressure-sensitive module 130 is connected to the analyzing module 240 and is configured to provide the sensor signal 132 (e.g. through a bound wire) to the analyzing module 240. Further, the emitter module 120 may be optionally connected to the analyzing module 240 so that the analyzing module 240 can trigger the emission of the light pulses 122 by the emitter module 120.

The emitter module 120, the pressure-sensitive module 130 and the analyzing module 240 are enclosed at the surface of the carrier substrate 110 by a cap, a lid or a housing 250. In other words, the lid 250 covers the pressure-sensitive module 130 (MEMS) and the analyzing module 240 (ASIC). Optionally also the emitter module 120 is covered delivering higher or larger back volume 204 as shown in FIG. 2. The lid 250 may be electrically-conductive (e.g. metal or metallized part or metal-filled polymer) and electrically connected to a ground contact to provide a shielding function. An electrical ground contact 212 of the shielding lid 250 to the substrate can be implemented on the carrier substrate 110 (e.g. solder or conductive adhesive). If the lid 250 provides the back volume (of the membrane of the pressure-sensitive module as shown in FIG. 2), the lid 250 may be acoustically sealed to the substrate (e.g. to avoid an excitation of the backside volume by the acoustic wave caused by the emitted light pulses).

The back volume 204 may be part of the reference gas volume 102 (e.g. connected to the front side volume by venting holes through the membrane, for example) or a volume separated from the reference gas volume 102. The carrier substrate 110 may comprise one or more electrical contacts 214 (e.g. solder ball or flat metallization or a bent metal part or through-hole contact or pin) in order to provide a connectability to other electronic devices.

The volume 104 intended to be filled with the gas to be analyzed and at least a part of the reference gas volume 102 are arranged at an opposite of the carrier substrate 110 with respect to the emitter module 120, the pressure-sensitive module 130 and the analyzing module 240. The volume 104 intended to be filled by the gas to be analyzed is enclosed by a housing 203 comprising a gas inlet 207 (e.g. for providing gas to be analyzed) and a gas outlet 205 (e.g. for draining of gas). In this way, a gas flow can be led through the volume 104 intended to be filled by the gas to be analyzed.

Alternatively, one hole (inlet and outlet) may be sufficient (e.g. for measuring environmental gases), which may be big enough to ensure reasonable exchange of gas in the volume 104, for example. In other words, a cavity (volume to be filled with a gas to be analyzed) may be formed by attaching a preformed part (e.g. housing) to the substrate (carrier substrate) providing a volume with gas to be measured, for example. The volume 104 intended to be filled by gas to be analyzed may be arranged opposite to the emitter module 120 so that the emitter module 120 can emit light pulses 122 through the hole or window 222 into the volume 104 intended to be filled with the gas to be analyzed.

The part of the reference gas volume 102 located opposite to the pressure-sensitive module 130 is enclosed by a housing 209 neighboring the housing 203 of the volume 104 intended to be filled with the gas to be analyzed. The housing 209 of the part of the reference gas volume 102 opposite to the pressure sensitive module 130 and the housing of the volume 104 intended to be filled by gas to be analyzed may be implemented by a common housing or by separate housings sharing a wall or comprising adjacent walls.

The carrier substrate 110 comprises a hole between the pressure-sensitive module 130 and the reference gas volume 102 at the opposite side representing an acoustic signal port so that acoustic waves caused at the opposite side of the pressure-sensitive module 130 can reach the pressure-sensitive module 130 through the hole 206.

The wall between the housing 209 of the reference gas volume 102 and the housing 203 of the volume 104 intended to be filled with the gas to be analyzed comprises at least partly a transparent region 202 being at least partly transparent for light within the frequency range of the light pulses 122 emitted by the emitter module 120. Further, the remaining inner walls of the housing 203 of the volume 104 intended to be filled with the gas to be analyzed comprise at least partly a surface (e.g. metal surface) reflecting at least a portion of the light pulses 122 emitted by the emitter module 120 so that the light pulses 122 or portions of the light pulses 122 not absorbed by the gas to be analyzed can reach the reference gas volume 102 through the transparent region 202.

FIG. 2 shows an implementation with a reference volume representing a concept for integration of a reference volume containing a defined gas (reference gas), for example. For example, this may be the gas which the sensor 200 is supposed to selectively detect. Absorption in the primary volume (volume to be filled with the gas to be analyzed) will then lead to no absorption in the reference volume and vice-versa, for example.

The reference gas may penetrate through so-called venting holes in the membrane. As a consequence, the back volume 204 can be filled with the reference gas. This may have a minor impact, especially, if the infrared beam (light pulses) does not directly hit the back volume 204. Then the pressure pulse (acoustic wave) causing the signal will not be created in the back volume 204, for example.

Figure 3:
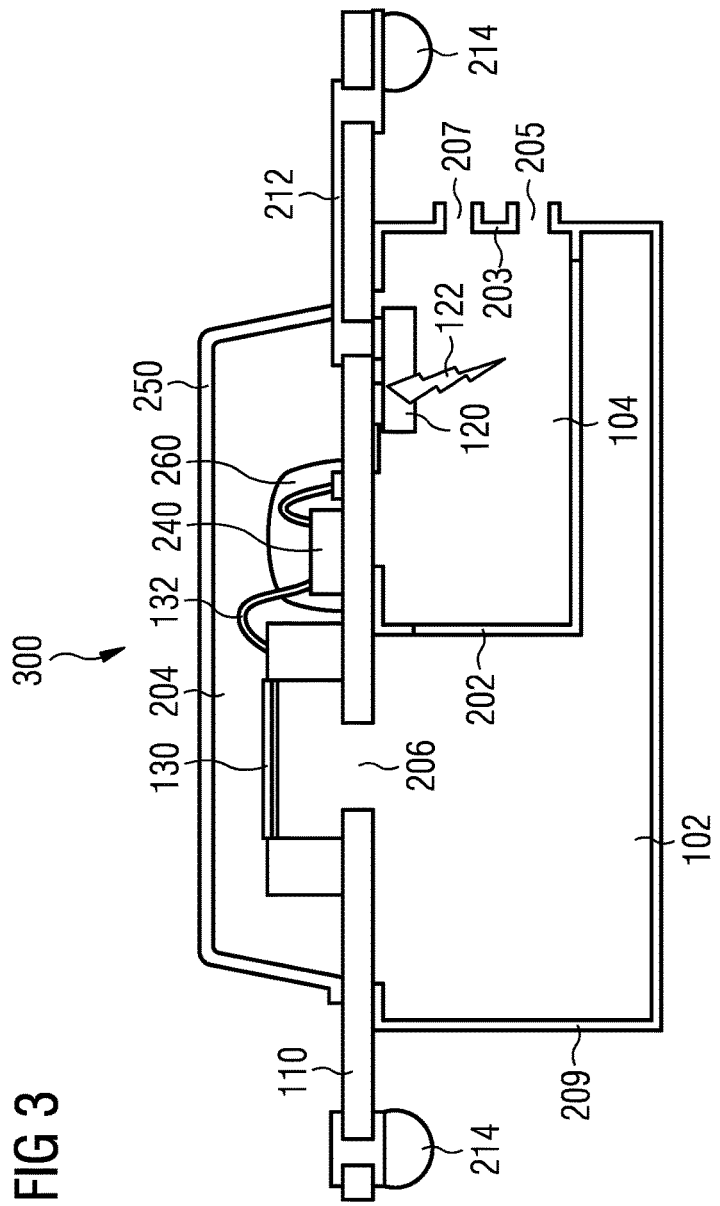

Alternatively, a large variety of different geometrically possible implementations may be used. FIG. 3 shows a schematic cross-section of a photoacoustic gas sensor device 300 according to an embodiment. The implementation of the photoacoustic gas sensor device 300 is similar to the implementation shown in FIG. 2. However, the emitter module 120 is arranged at a side of the carrier substrate 110 opposite to the pressure-sensitive module 130 and the analyzing module 240. Further, the emitter module 120 is arranged within the volume 104 intended to be filled with the gas to be analyzed. Further details and aspects are explained in connection with FIGS. 1 and 2.

Figure 4:
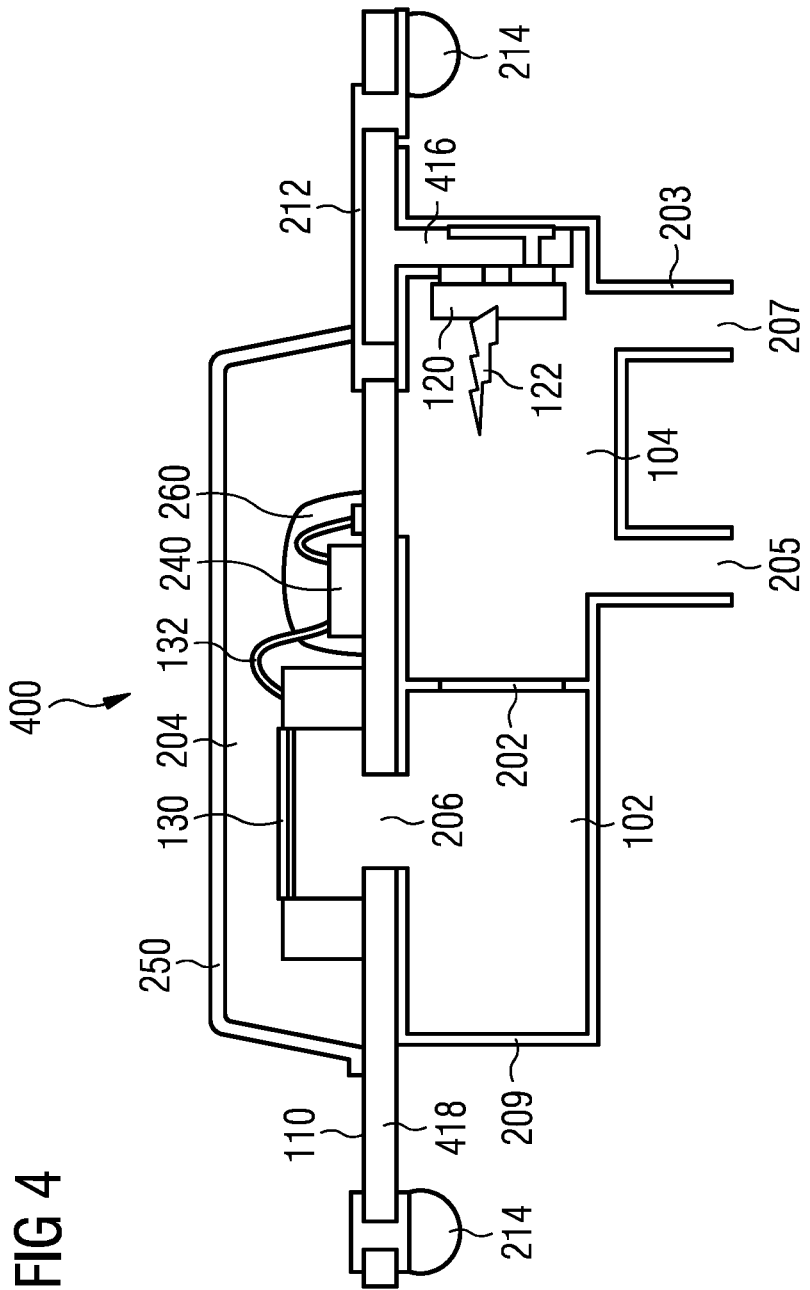

FIG. 4 shows a schematic cross-section of a photoacoustic gas sensor device 400 according to an embodiment. The implementation of the photoacoustic gas sensor device 400 is similar to the implementations shown in FIGS. 2 and 3. However, the carrier substrate 110 deviates from the basically flat geometry and comprises at least an L-shaped geometry (or a T-shaped geometry). The emitter module is arranged at a first leg 416 (e.g. the short leg) of the L-shaped geometry of the carrier substrate 110 within the volume 104 intended to be filled with the gas to be analyzed. Further, the pressure-sensitive module 130 and the analyzing module 240 are arranged at the second leg 418 (e.g. the long leg) of the L-shaped geometry of the carrier substrate 110. In this way, the emitter module 120 can be arranged so that the emitted light pulses 120 are directed in the direction of the transparent portion 202 of the wall between the reference gas volume 102 and the volume 104 intended to be filled with the gas to be analyzed. Further details and aspects are described in connection with FIGS. 1 to 3.

The transparent portion 202 may be a wall with low infrared absorption (e.g. silicon, silicon oxide or germanium). The one or more walls may optionally be covered with an anti-refraction material for infrared radiation (IR). The other walls may be implemented by or made out of metal or metallized plastic. A high reflection of the infrared beam may help in creating a good signal.

Figure 5:
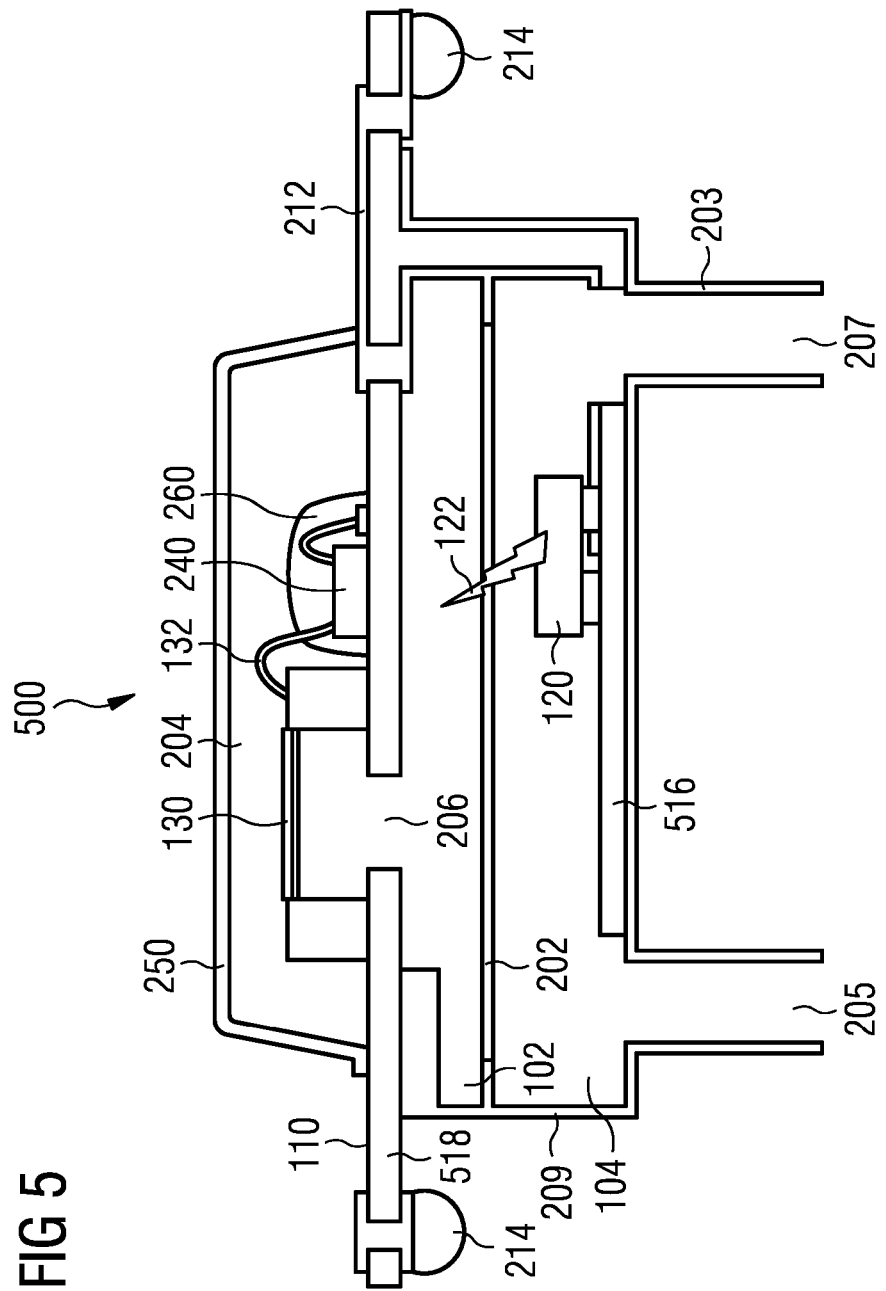

FIG. 5 shows a schematic cross-section of a photoacoustic gas sensor device 500 according to an embodiment. The implementation of the photoacoustic gas sensor device 500 is similar to the implementations shown in FIGS. 2 to 4. However, the carrier substrate 110 comprises an at least U-shaped geometry (e.g. in this example a U-shape with unequally long legs and an extension of the longer leg). In other words, the carrier substrate 110 comprises two parallel portions (legs of the U-shape) connected by a portion arranged orthogonal to the two parallel portions (bottom of the U-shape). The emitter module 120 is arranged at the first leg 516 of the U-shaped geometry of the carrier substrate 110 and the pressure-sensitive module 130 and the analyzing module 240 are arranged at a second leg 518 of the U-shaped geometry of the carrier substrate 110. The emitter module 120 is located on a side of the first leg 516 facing the second leg 518. The pressure-sensitive module 130 and the analyzing module 240 are arranged on a side of the second leg 518 opposite to the first leg 516. The gap between the first leg 516 and the second leg 518 is divided by a wall of the housing 209 of the reference gas volume 102 and the housing 203 of the volume 104 intended to be filled with the gas to be analyzed, separating the reference gas volume 102 and the volume 104 intended to be filled with the gas to be analyzed. Further details and aspects are described in connection with FIGS. 1 to 4.

Figure 6:
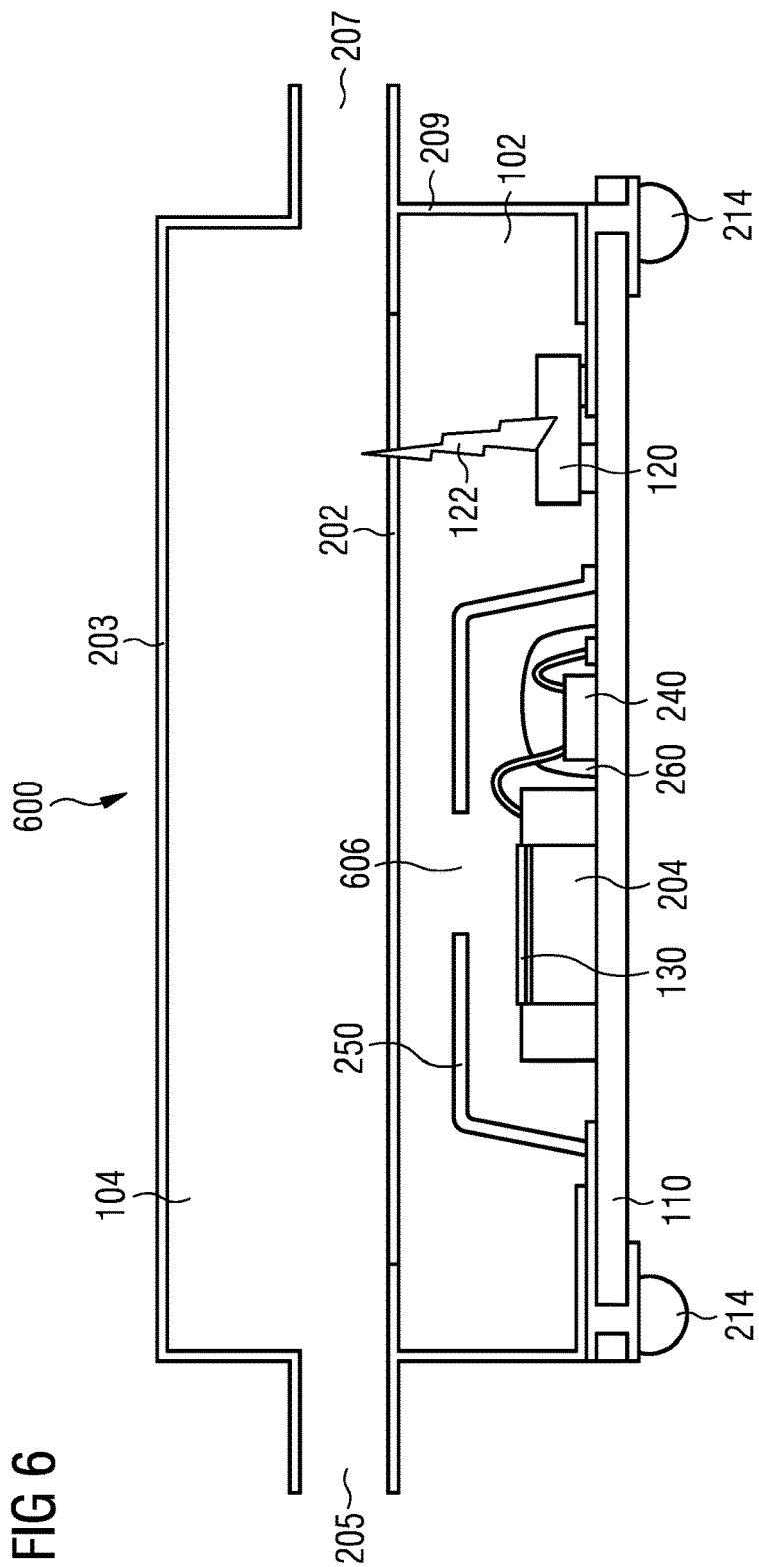

FIG. 6 shows a schematic cross-section of a photoacoustic gas sensor device 600 according to an embodiment. The implementation of the photoacoustic gas sensor device 600 is similar to the implementation shown in FIG. 2. However, the emitter module 120, the pressure-sensitive module 130, the analyzing module 240, the reference gas volume 102 and the volume 104 intended to be filled with the gas to be analyzed are arranged on the same side of the basically flat carrier substrate 110. Instead of the hole 206 through the carrier substrate 110, the cap or lid 250 comprises a hole 606 in order to provide access to the pressure-sensitive module 130. The emitter module 120 is arranged outside the lid 250 (covering the pressure-sensitive module and the analyzing module), but within the reference gas volume 102. The housing 209 of the reference gas volume 102 surrounds the lid 250 as well as the emitter module 120. The housing 209 of the reference gas volume 102 comprise a wall being arranged basically in parallel to the carrier substrate 110 separating the reference gas volume 102 from the volume 104 intended to be filled by a gas to be analyzed comprising a transparent portion 202. The housing 203 of the volume 104 intended to be filled by a gas to be analyzed is arranged opposite to the transparent portion 202. The emitter module 120 can emit light pulses 122 through the reference gas volume 102 and the transparent portion 202 into the volume 104 to be filled with a gas to be analyzed. Non-absorbed light pulses can be reflected by the walls of the housing 203 back into the reference gas volume 102 and can be absorbed by the reference gas causing an acoustic wave detectable by the pressure-sensitive module 130. In this example, the back volume 204 of the pressure-sensitive module 130 is located between a membrane of the pressure-sensitive module 130 and the carrier substrate 110 and is separated from the reference gas volume 102 (e.g. via an impermeable membrane). Further details and aspects are described in connection with FIGS. 1 and 2.

FIG. 6 shows a version with top access to a microphone or pressure-sensitive module. In other words, a sensor with a top acoustic port with reference volume for reference gas can be implemented.

In comparison to the example shown in FIGS. 2 to 5, the emitter module 120 is arranged so that light pulses 122 emitted by the emitter module 120 reach the reference gas volume 102 after crossing a part of the reference gas volume 102 and crossing the volume 104 intended to be filled with the gas to be analyzed, while in FIGS. 2 to 5 the emitter module 120 is arranged so that light pulses 122 emitted by the emitter module 120 reach the reference gas volume 102 after only crossing the volume 104 intended to be filled with the gas to be analyzed (as well as the transparent portion of the housing), but no other gas.

In some embodiments, a photoacoustic gas sensor device comprises more than one reference gas volume. In this way, a gas can be analyzed with regard to more than one component with high accuracy.

In other words, a photoacoustic gas sensor device may comprise at least a second reference gas volume separated from the first reference gas volume and separated from the volume intended to be filled with a gas to be analyzed.

FIG. 7 shows a schematic illustration of a photoacoustic gas sensor device 700 according to an embodiment. The implementation of the photoacoustic gas sensor device 700 is similar to the implementation shown in FIG. 1. However, additionally to the first reference gas volume 102 with the first pressure-sensitive module 130, the photoacoustic gas sensor device 700 comprises a second reference gas volume 704 with a second pressure-sensitive module 730 and a third reference gas volume 706 with a third pressure-sensitive module 740.

The emitter module 120 is implemented by a thermal infrared emitter comprising an emitter element 722 electrically connected to a pulsed voltage or current source 724. By pulsing the current flow through the emitter element 722, infrared pulses in a broad frequency range with defined temporal characteristic are emitted. In other words, the emitter module 120 represents an electrically-chopped broadband infrared emitter, for example.

The emitted infrared light pulses cross a volume 104 to be filled with a gas mixture (e.g. components A, B and C) to be analyzed before entering one of the reference gas volumes through a transparent portion of the housings of the reference gas volumes. The non-absorbed portion of the infrared light pulses reaching the respective reference gas volume can cause an acoustic wave by interacting with the reference gas in the respective reference gas volume. This acoustic wave can be detected by the respective pressure-sensitive module (e.g. implemented by a microphone module) providing a sensor signal comprising information on the acoustic wave.

The second pressure-sensitive module 730 and the third pressure-sensitive module 740 may be arranged also on the common carrier substrate (not shown). The second pressures-sensitive module 730 is arranged within the second reference gas volume 704 and the third pressure-sensitive module 740 is arranged within the third reference gas volume 706.

In this example, the gas to be analyzed comprises at least components A, B and C and the first reference gas volume 102 is filled with gas A, the second reference gas volume 704 is filled with gas B and the third reference gas volume 706 is filled with gas C. The gas to be analyzed comprises a large portion of component C, a medium portion of gas A and a small portion of gas B. Consequently, infrared light with a wavelength absorbed by component C is nearly completely absorbed already by the gas to be analyzed, while infrared light with a wavelength absorbed by component B is hardly absorbed by the gas to be analyzed. Therefore, nearly no light pulses in the frequency range absorbable by gas C reaches the third reference gas volume 706 and nearly the whole portion of the light pulses comprising a frequency range absorbable by gas B reaches the second reference gas volume 704 and causes corresponding acoustic waves. Consequently, the sensor signal 742 provided by the third pressure-sensitive module 730 comprises a small amplitude compared to the sensor signal 732 of the second pressure-sensitive module 730, comprising a large signal amplitude. The respective sensor signals are shown by schematic diagrams indicating the voltage V of the sensor signals over time T. The diagrams further indicated a maximal signal amplitude 702, if no absorption occurs by the gas to be analyzed.

In other words, FIG. 7 shows an example of one broadband thermal infrared sensor which is chopped and illuminates three different reference cells with respective microphones giving a specific signal on each gas concentration, for example.

The different reference gas volumes can be arranged in various ways. For example, the emitter module is arranged so that light pulses emitted by the emitter module 120 reach the second reference gas volume 704 after crossing the volume 104 intended to be filled with the gas to be analyzed and after crossing the first reference gas volume 102.

Figure 8A:
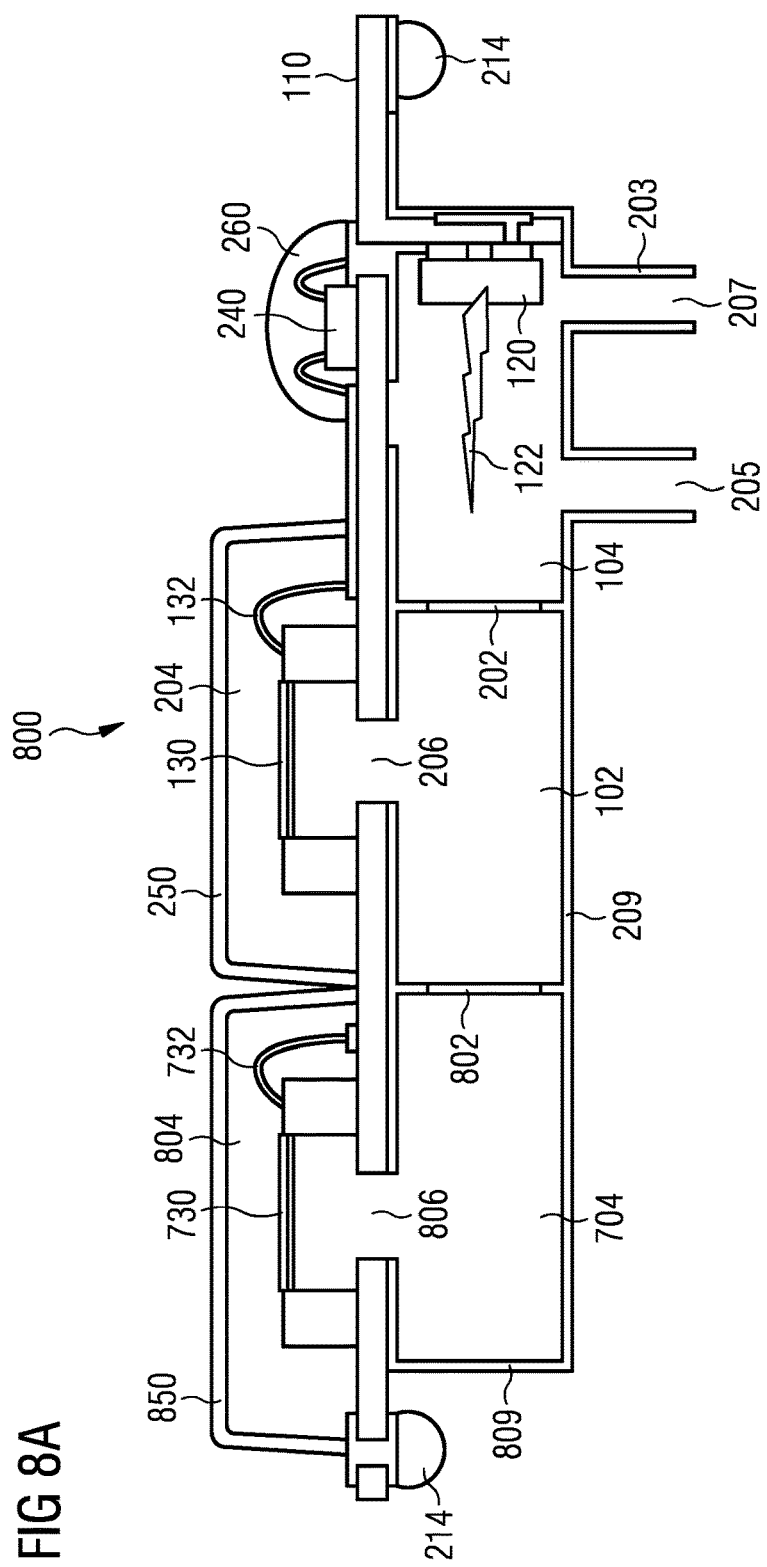

FIG. 8A shows a schematic cross-section of a photoacoustic gas sensor device 800 according to an embodiment. The implementation of the photoacoustic gas sensor device 800 is similar to the implementation shown in FIG. 4. However, a second reference gas volume 704 is arranged laterally adjacent to the first reference gas volume 102 and a second pressure-sensitive module 730 is arranged laterally adjacent to the first pressure-sensitive module 130. The second reference gas volume 704 and the second pressure-sensitive module 730 are arranged on opposite sides of the carrier substrate with a hole 806 representing an acoustic port through the carrier substrate 110 in between. In this example, the analyzing module 140 is arranged outside the cap or lid 250 covering the first pressures-sensitive module 130. Correspondingly, the second pressure-sensitive module 730 is covered by a second cap or lid 850. Alternatively, the first lid 250 and the second lid 850 are implemented in one piece. The second reference gas volume 704 is surrounded by a housing 809 adjacent to the housing 209 of the first reference gas volume 102 separated by a wall with a transparent portion 802 (e.g. at least partly transparent for a frequency range of the light pulses to be absorbed by the reference gas within the second reference gas volumes). Alternatively, the volume 104 intended to be filled with a gas to be analyzed, the reference gas volume 102 and the second reference gas volume 704 may be separated by a common housing comprising corresponding walls in between.

The backside volume 804 of the second pressure-sensitive module 730 is implemented corresponding to the backside volume 204 of the first pressure-sensitive module 130. Further details and aspects are described in connection with FIGS. 1 and 4, for example.

FIG. 8A shows a version with two or more microphones, for example. An example for a sensor with two (or more) microphone chips and a respective number of reference volumes is shown, for example. This may enable selectivity of the sensor to more than one gaseous material. In this way, a selectivity for various kinds of gases is possible. Each microphone die can be connected to its analyzing module ASIC (FIG. 8A shows a version with only one ASIC serving the whole module). Alternatively, versions with different geometry (e.g. FIGS. 2 to 6) are possible.

Figure 8B:
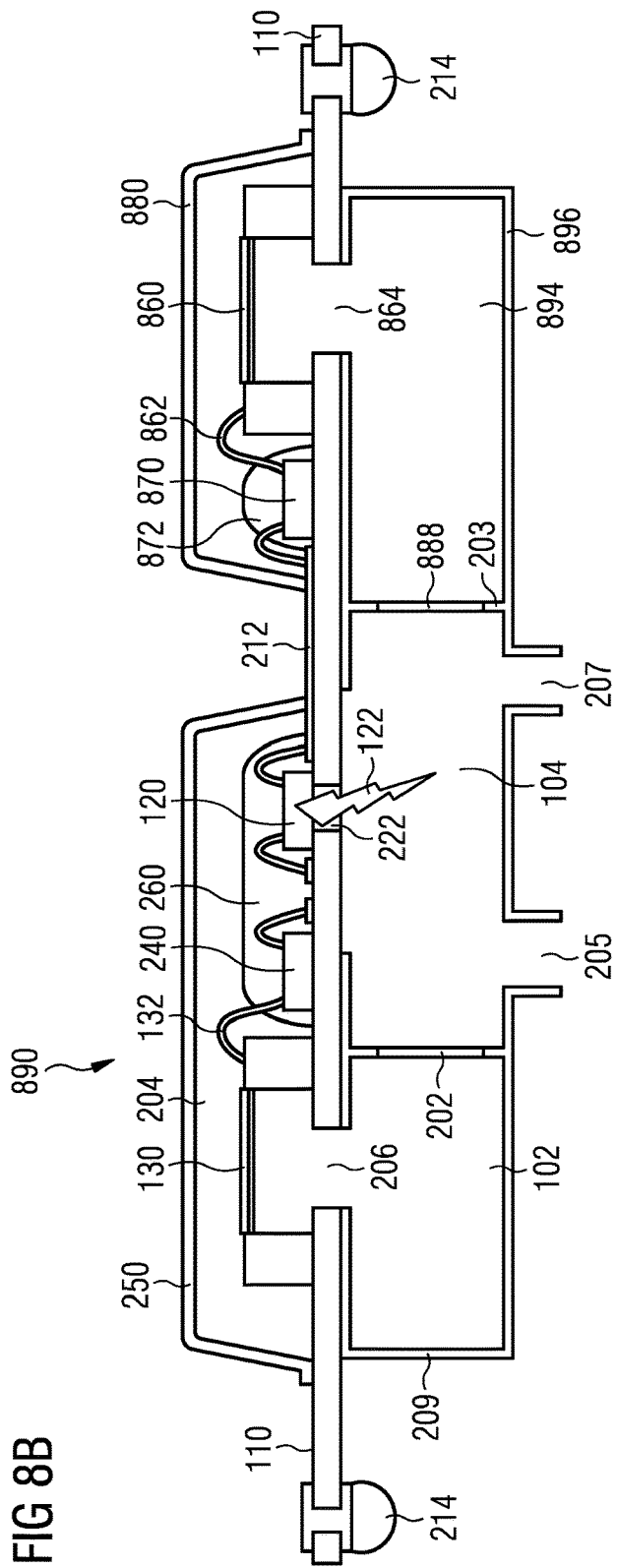

FIG. 8B shows a schematic cross-section of a photoacoustic gas sensor device 890 according to an embodiment. The implementation of the photoacoustic gas sensor device 890 is similar to the implementation shown in FIG. 2. However, the photoacoustic gas sensor device 890 comprises a second reference volume 894 arranged at a side of the of the volume 104 intended to be filled with the gas to be analyzed opposite to the first reference volume 102. The wall between the housing 896 of the second reference gas volume 894 and the housing 203 of the volume 104 intended to be filled with the gas to be analyzed comprises at least partly a transparent region 888 being at least partly transparent for light within the frequency range of the light pulses 122 emitted by the emitter module 120. Further, the remaining inner walls of the housing 203 of the volume 104 intended to be filled with the gas to be analyzed comprise at least partly a surface (e.g. metal surface) reflecting at least a portion of the light pulses 122 emitted by the emitter module 120 so that the light pulses 122 or portions of the light pulses 122 not absorbed by the gas to be analyzed can reach the first reference gas volume 102 through the transparent region 202 or the second reference gas volume 894 through the transparent region 888.

Further, the photoacoustic gas sensor device 890 comprises a second analyzing module 870 laterally arranged next to a second pressure-sensitive module 860 on the same side of the carrier substrate 110 as the first pressure-sensitive module 130. The second analyzing module 870 may be implemented as a logic die (comprising logical electrical circuits) for signal conditioning or determining information on the gas to be analyzed based on a sensor signal 862 provided by the second pressure-sensitive module 860, for example. The second analyzing module 870 may be covered by casting compound 872 (e.g. epoxy). The second pressure-sensitive module 860 and the second analyzing module 870 are enclosed by a second cap 880. The carrier comprises a hole 864 between the second reference gas volume 894 and the second pressure-sensitive module 860 so that acoustic waves caused at the opposite side of the second pressure-sensitive module 860 can reach the second pressure-sensitive module 860 through the hole 864.

FIG. 9 shows a schematic cross-section of a photoacoustic gas sensor device 900 according to an embodiment. The implementation of the photoacoustic gas sensor device 900 is similar to the implementation shown in FIG. 8A. However, only one pressure-sensitive module 130 is arranged opposite to the second reference gas volume 704. This pressure-sensitive gas module 130 detects acoustic waves caused by light pulses not absorbed by the gas to be analyzed and the first reference gas within the first reference gas volume 102. More details and aspects are described in connection with FIGS. 1, 4 and 8, for example.

FIG. 9 shows a version with two reference volumes and only one microphone or an example for a sensor with just one microphone chip and two (or more) reference volumes. Specific combinations of reference volumes, reference gases, microphones and (broadband or narrowband) IR-emitters can be used to create specific signals and to implement selectivity for one or more gaseous materials, for example.

Some embodiment relate to a photoacoustic gas sensor device comprising more than one emitter module. For example, a photoacoustic gas sensor device comprises a second emitter module (or more) arranged on the carrier substrate and configured to emit light pulses. The second emitter module can be arranged so that light pulses emitted by the second emitter module reach the second reference gas volume after crossing the volume intended to be filled with the gas to be analyzed. In this way, the frequency characteristic of the emitted light pulses can be adapted to the components to be detected within the gas to be analyzed. For example, the first emitter module emits light pulses within a narrow frequency range adapted to the first reference gas within the first reference gas volume and the second emitter module emits light in a second narrow frequency range adapted to a second reference gas within the second reference gas volume.

FIG. 10 shows a schematic cross-section of a photoacoustic gas sensor device 1000 according to an embodiment. The implementation of the photoacoustic gas sensor device 1000 is similar to a combination of the implementations shown in FIGS. 5 and 8. A basically U-shaped carrier substrate 110 is used and two reference gas volumes are arranged in the gap between the legs of the U-shape. Additionally, the photoacoustic gas sensor device 1000 comprises a second emitter module 1020 arranged on the first leg 516 of the U-shape laterally adjacent to the first emitter module 120 and facing a transparent portion 1002 of the housing 809 of the second reference gas volume 704. The analyzing module 240 is arranged at a bottom portion of the U-shaped geometry of the carrier substrate 110. In other words, the photoacoustic gas sensor device 1000 comprises a second emitter module 1020 arranged on the carrier substrate 110 and configured to emit light pulses. This second emitter module 1020 is arranged so that light pulses emitted by the second emitter module 1020 reach the second reference gas volume 704 after crossing the volume 104 intended to be filled with a gas to be analyzed. More details and aspects are described in connection with FIG. 1, FIG. 5 and FIG. 8, for example.

FIG. 10 shows a version with two or more IR-emitters or an example for a sensor with two (or more) IR-emitters. They can be combined with one or more (or no reference volumes according to FIG. 12). The example shows a combination of two emitters with two reference volumes. An implementation with no reference volumes may make sense as soon as the IR-emitters differ in their emission spectrum (either a narrow frequency band which selectively causes specific excitations in specific gases or broader spectra leading to various excitation modes in various gaseous materials), for example.

FIG. 11 shows a schematic cross-section of a photoacoustic gas sensor device 1100 according to an embodiment. The implementation of the photoacoustic gas sensor device 1100 is similar to the implementation shown in FIG. 11. However, the photoacoustic gas sensor device 1100 comprises a third emitter module 1120 arranged on the first leg 516 of the at least U-shaped carrier substrate 110 (bottom of the U-shape, not shown) and a third pressure-sensitive module 740 arranged within a third reference gas volume 706 arranged on the second leg 518 of the at least U-shaped geometry of the carrier substrate 110. Further, the reference gas volumes are arranged on the same side as the pressure-sensitive modules on the second leg 518 of the at least U-shaped geometry of the carrier substrate 110. The second leg 518 of the carrier substrate 110 comprises windows (e.g. with low absorption for infrared light) arranged opposite to the emitter modules on the first leg 516 of the at least U-shaped geometry (e.g. the U-shaped geometry may be also closed at the other end resulting in an O-shaped geometry) so that light pulses emitted by the emitter modules can reach the respective reference gas volume through the volume 104 intended to be filled with the gas to be analyzed and the respective window 222, 1122, 1124. More details and aspects are described in connection with FIG. 10, for example.

FIG. 11 illustrates one broadband thermal infrared sensor illuminating three different reference cells with respective microphones, for example. For example, an infrared heater (e.g. integrated in a printed circuit board or micro electromechanical system heater) is arranged on the carrier substrate. Further, the reference gas volumes are separated from each other by a cap (e.g. metal) arranged on the carrier substrate. A gas channel for the gas to be analyzed may be arranged between two legs of a U-shaped or O-shaped carrier substrate (e.g. implemented by two printed circuit boards arranged parallel to each other and connected through orthogonal portions). Due to the laterally-shifted arrangement of the emitter modules and the pressure-sensitive modules, a direct illumination of the backside volume through the membrane of the pressure-sensitive modules by the light pulses emitted by the emitter modules can be avoided or significantly reduced.

Alternatively, a single emitter module may comprise more than one emitter element distributed over the carrier substrate (e.g. FIG. 11).

Figure 12:
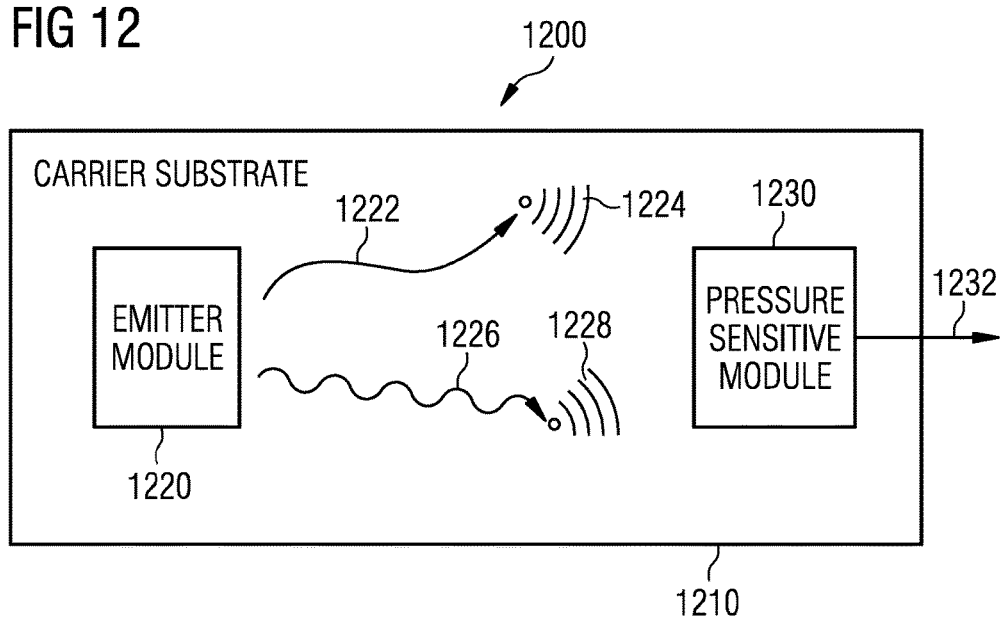
FIG. 12 shows a schematic illustration of a photoacoustic gas sensor device.

FIG. 12 shows a schematic illustration of a photoacoustic gas sensor device 1200 for analyzing gas according to an embodiment. The photoacoustic gas sensor device 1200 comprises an emitter module 1220 and a pressure-sensitive module 1230 arranged on a common carrier substrate 1210. The emitter module 1220 is configured to emit first light pulses 1222 with a first frequency range and with a first temporal occurrence characteristic and second light pulses 1226 within a second frequency range and with a second temporal occurrence characteristic. The pressure-sensitive module 1230 generates a sensor signal 1232 indicating information on first acoustic waves 1224 caused by the first light pulses 1222 emitted by the emitter module 1220 interacting with a gas to be analyzed and second acoustic waves 1228 caused by the second light pulses 1226 emitted by the emitter module 1220 interacting with the gas to be analyzed.

By using an emitter module capable of emitting light pulses within different frequency ranges and with different temporal occurrence characteristics, an absorption of portions of the light pulses at different gas components can be excited so that different components of a gas can be analyzed simultaneously. Due to the different temporal occurrence characteristics, the acoustic waves caused by the different light pulses can be differentiated from each other within the sensor signal 1232.

The photoacoustic gas sensor device 1200 is a device capable of analyzing gas based on the photoacoustic effect. For this, the photoacoustic gas sensor device 1200 comprises an emitter module 1220 for generating light pulses to be absorbed by a gas in order to cause an acoustic wave and a pressure-sensitive module 1230 for detecting the acoustic wave and generating a corresponding sensor signal 1232.

The emitter module 1220 and the pressure-sensitive module 1230 are arranged on a common carrier substrate 110. In this connection, the carrier substrate 1210 may be a semiconductor die comprising an emitter circuitry or emitter structure representing the emitter module 1220 and a pressure-sensitive circuitry or pressure-sensitive structure representing the pressure sensitive module 1230, for example.

Alternatively, the carrier substrate 1210 may be a structured substrate (e.g. organic like a printed circuit board PCB, a metal grid like a lead frame or a flex board) providing a surface for mounting the emitter module 1220 implemented by a surface-mounted device SMD (e.g. semiconductor die) and the pressure-sensitive module 1230 implemented on another or the same surface-mounted device, for example.

In other words, the emitter module 1220 and the pressure-sensitive module 1230 may be implemented on the same semiconductor die representing the carrier substrate 1210 or the pressure-sensitive module 1230 and the emitter module 1220 are implemented on different semiconductor dies mounted on a common carrier substrate 1210, for example.

The emitter module 1220 is configured to emit light pulses. These light pulses may comprise frequency portions in only two or more narrow frequency bands. The emitter module 1220 may comprise two or more emitter elements for emitting light pulses with different frequency portions or an emitter element capable of emitting light pulses with different frequency portions. For example, the emitter module 1220 may comprise a thermal emitter element provided with varying currents or voltages so that the emitter element comprises different temperatures at different times or the thermal emitter element comprises a geometry with laterally varying shape resulting in a lateral varying current densities and consequently varying temperatures.

For example, the light pulses generated by the emitter module 1220 may comprise frequency portions within the infrared frequency region (e.g. 780 nm to 1 mm or between 300 GHz and 400 THz) or visible frequency region. Alternatively, the emitter module 1220 may emit light pulses within a narrow frequency band adjusted to the gas to be analyzed or a component of the gas to be analyzed (e.g. for selectively exciting an absorption within the gas to be analyzed).

Further, the emitter module 1220 can generate the light pulses with a predefined temporal characteristic. For example, the light pulses can be obtained by varying the light intensity of the emitted light (e.g. by modulating the light or by generating single flashes of light). For example, the emitter module 1220 may be triggered periodically causing light pulses with predefined time intervals in between or with a predefined temporal frequency.

The emitter module 1220 may be implemented in various ways. For example, the emitter module 1220 may comprise a thermal emitter element, a photodiode element or a laser diode (e.g. infrared diode or infrared laser diode).

The pressure-sensitive module 1230 is configured to generate a signal indicating information on a pressure or pressure variation applied to the pressure-sensitive module 1230, for example. For example, the pressure-sensitive module 1230 may comprise a membrane (e.g. of a microphone structure) or a piezoelectric element. The pressure applied to the membrane or the piezoelectric element may cause a signal with a voltage or a current proportional to the applied pressure, a pressure variation or a pressure difference of time, for example. If a light pulse or a portion of a light pulse emitted by the emitter module 1220 is absorbed by the gas to be analyzed, an acoustic wave is excited or generated. This acoustic wave propagates through the gas and reaches the pressure-sensitive module 1230. This acoustic wave causes a pressure variation at the pressure-sensitive module 1230 so that the pressure-sensitive module 1230 can generate the sensor signal 1232 indicating information on the acoustic wave. This information may be a voltage or a current proportional to the pressure or a pressure variation caused by the acoustic wave, for example. The strength of the acoustic wave may be proportional to the amount of light absorbed by the gas.

The volume intended to be filled with the gas to be analyzed can be an open volume (e.g. free access to the photoacoustic gas sensor device for gas in the proximity of the photoacoustic gas sensor device) or may be an encapsulated volume with a gas inlet and a gas outlet, for example.

The emitter module 1220 may be arranged within the volume intended to be filled with the gas to be analyzed. Alternatively, the emitter module 1220 may be separated from the volume intended to be filled with the gas to be analyzed.

As already mentioned, the pressure-sensitive module 130 may comprise optionally at least a membrane. This membrane may be moved by an acoustic wave caused by light pulses emitted by the emitter module 120 interacting with a gas.

Optionally, the emitter module 1220 and the pressure-sensitive module 1230 can be arranged so that at least a volume located at one side (e.g. backside) of the membrane cannot be reached by light pulses emitted by the emitter module 120 or so that less than 1% (or less than 10%, less than 5% or less than 0.1%) of the light pulses or portions of the light pulses emitted by the emitter module 120 is able to reach the volume located at the one side (e.g. backside) of the membrane. In other words, the emitter module 1220 and/or the pressure-sensitive module 1230, the carrier substrate 1210 and/or a part of the package of the photoacoustic gas sensor device 1200 may provide the possibility of avoiding light emitted by the emitter module 1220 reaching a backside of the membrane of the pressure-sensitive module 1230, for example. In this way, an acoustic wave can be only caused at one side of the membrane (e.g. at the front side of the membrane) so that a destructive interference with acoustic waves caused at the other side of the membrane can be avoided resulting in a large pressure variation at the membrane caused by absorbed light pulses.

Additionally, alternatively or optionally to one or more aspects mentioned above, the photoacoustic gas sensor device 1200 may comprise an analyzing module configured to determine information on the gas to be analyzed based on the sensor signal 1232. The analyzing module may comprise an electric circuit implemented together with the pressure-sensitive module 1230 on the same semiconductor die. Alternatively, the analyzing module may be arranged on the carrier substrate 1210 and implemented on a different semiconductor die than the pressure-sensitive module 1230. In this way, the manufacturing processes and/or technologies may be better adapted to the requirements of the pressure-sensitive module 1230 and the analyzing module respectively. For example, the analyzing module may be implemented in an easily scalable CMOS-technology (Complementary Metal Oxide Semiconductor), while the pressure-sensitive module may be implemented by an MEMS technology (Micro Electro Mechanical System) suitable for manufacturing movable parts (e.g. a membrane).

For example, the first light pulses are emitted with a first time distance between two succeeding light pulses and the second light pulses are emitted with a second time distance between succeeding light pulses. The time distance between succeeding light pulses may vary within the frequency range detectable by the pressure-sensitive module (e.g. between 5 Hz and 10000 Hz or 10 Hz and 1000 Hz). For example, the emitter module may emit the first light pulses 1222 with a time distance of less than 20 ms (corresponding to a frequency of 50 Hz) representing the first temporal occurrence characteristic and the second light pulses 1226 with a time distance of more than 20 ms representing the second temporal occurrence characteristic (or 5 ms, 10 ms, 100 ms or 1000 ms). In this way, the acoustic waves caused by the different light pulses can be easily differentiated by the pressure-sensitive module 1230 or an analyzing module processing the sensor signal 1232.

Figure 13:
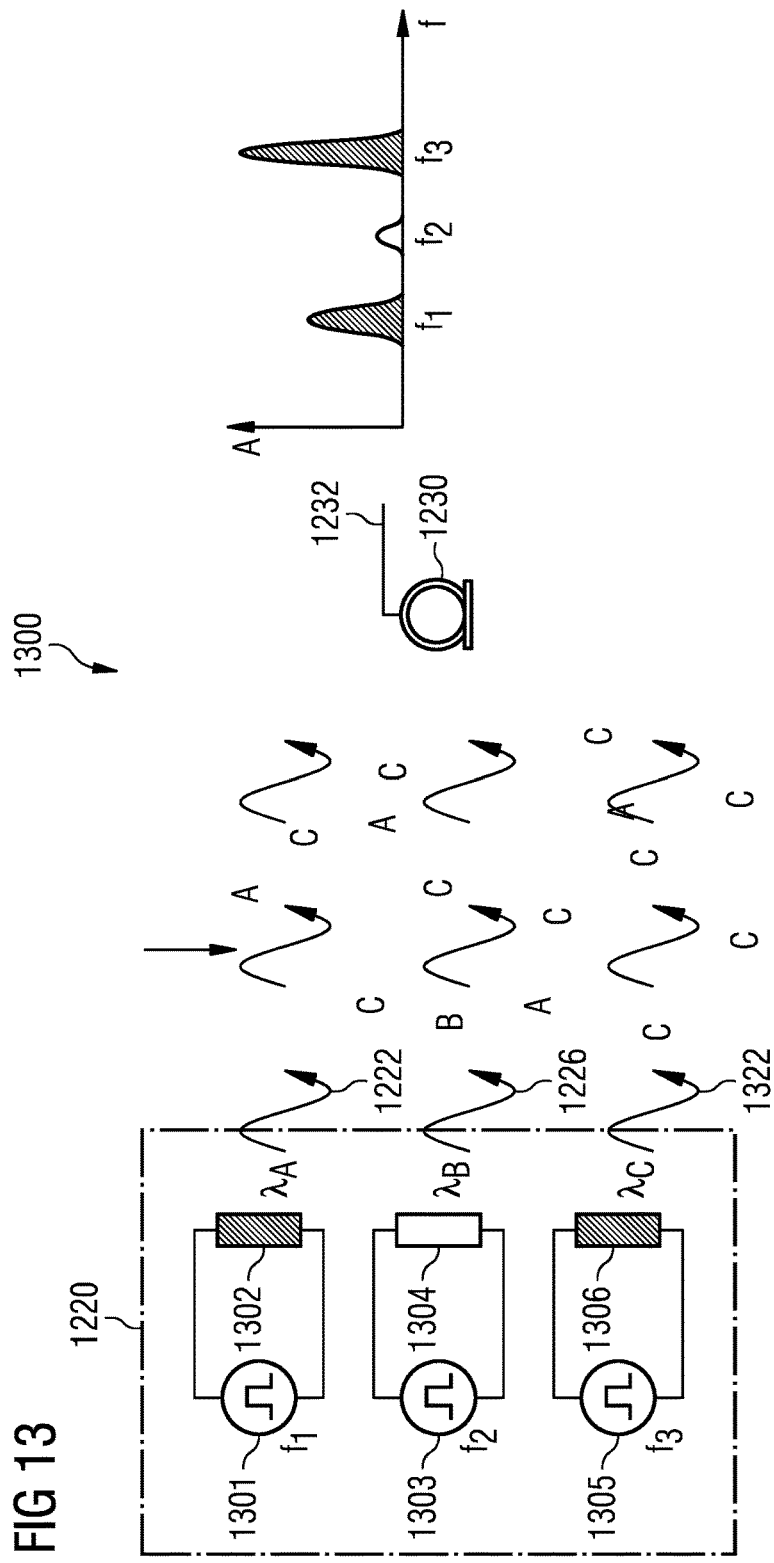
FIG. 13 shows a schematic illustration of a further photoacoustic gas sensor device.

FIG. 13 shows a schematic illustration of a photoacoustic gas sensor device 1300 according to an embodiment. The implementation of the photoacoustic gas sensor device 1300 is similar to the implementation shown in FIG. 12. However, the emitter module 1220 emits third light pulses 1322 within a third frequency range and a third temporal occurrence characteristic. The emitter module 1220 comprises a first narrowband infrared emitter element 1302 (e.g. photodiode, laser diode or terminal emitter with bandpass filter) triggered by a pulsed voltage or current source 1301 causing first light pulses with a wavelength of $\lambda_A$ with a first temporal frequency $f_1$. The emitter module 1220 comprises a second narrowband infrared emitter element 1304 triggered by a pulsed voltage or current source 1303 causing second light pulses with a wavelength of $\lambda_B$ with a first temporal frequency $f_2$. Further, the emitter module 1220 comprises a third narrowband infrared emitter element 1306 triggered by a pulsed voltage or current source 1305 causing third light pulses with a wavelength of $\lambda_C$ with a first temporal frequency $f_3$.

The first wavelength $\lambda_A$ may be adapted to an absorption of a first component A of a gas to be analyzed, the second wavelength $\lambda_B$ may be adapted to an absorption of a second component B of the gas to be analyzed and the third wavelength $\lambda_C$ may be adapted to an absorption of a third component C of the gas to be analyzed. The pressure-sensitive module 1230 detects acoustic waves caused by the different light pulses with different temporal occurrence characteristics corresponding to the respective trigger frequency so that the sensor signal 1232 comprises signal portions with different frequencies as illustrated by the diagram indicating the signal amplitude A over frequency f of the sensor signal 1232.

In this example, the gas to be analyzed comprises at least components A, B and C. The gas to be analyzed comprises a large portion of component C, a medium portion of gas A and a small portion of gas B. Consequently, infrared light with a wavelength absorbed by component C is nearly completely absorbed already by the gas to be analyzed, while infrared light with a wavelength absorbed by component B is hardly absorbed by the gas to be analyzed. The corresponding sensor signal 1232 is shown by the schematic diagram indicating the amplitude A of the sensor signals over the frequency f.

FIG. 13 shows different infrared (IR) sources designed such that they have narrowband emission fitting to the gas to be detected, for example. Each infrared source may be chopped with a special frequency that can be clearly distinguished by one microphone (pressure-sensitive module). With a frequency analysis of the microphone spectrum (sensor signal) the gases can be distinguished and analyzed in concentration. This can be done without a reference gas volume or a reference cell.

A sensor device 1300 may use an electrically chopped narrowband infrared emitter (e.g. photonic designed or combination of broadband emitter plus bandpass filter). The acoustic effect of just heating air can be calibrated, for example. Alternatively, one emitter can be swept to different infrared wavelengths and chopped with different audio wavelengths, for example.

Figure 14:
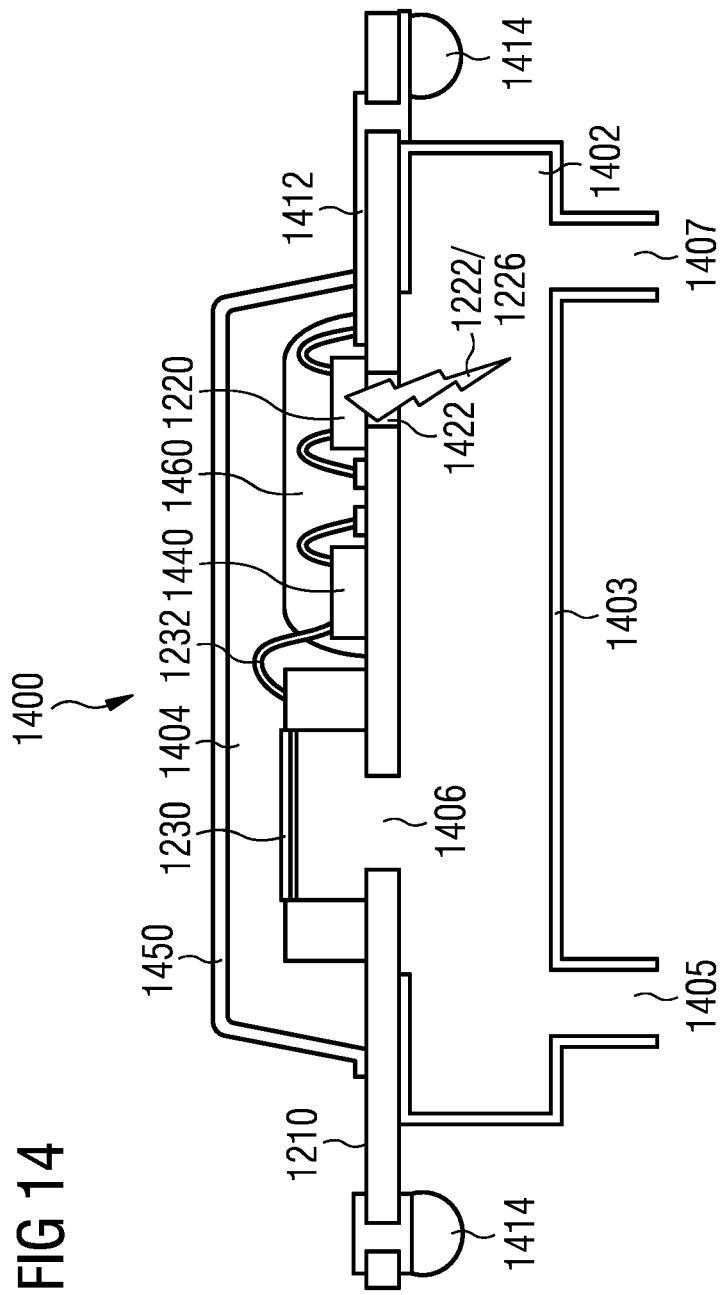

FIG. 14 shows a schematic cross section of a photoacoustic gas sensor device 1400 according to an embodiment. The implementation of the photoacoustic gas sensor device 1400 is similar to the implementation shown in FIG. 12 or FIG. 13. An emitter module 1220, a pressure-sensitive module 1230 and an analyzing module 1440 are arranged on the same side of a carrier substrate 1210.

The carrier substrate 1210 is for example a structured substrate (e.g. organic printed circuit board, a metal grid or lead frame).

The emitter module 1220 is an infrared IR emitter (e.g. IR-diode or laser diode) and can be assembled as chip (as shown in FIG. 14) or as complete packaged component, for example.

The analyzing module 1440 may be implemented as a logic die (comprising logical electrical circuits) for signal conditioning or determining information on the gas to be analyzed based on the sensor signal 1232 provided by the pressure-sensitive module 1230, for example. The analyzing module 1440 can be implemented by an application-specific integrated circuit (ASIC), for example.

The carrier substrate 1210 comprises a basically flat geometry (e.g. neglecting topology or unevenness due to metal layers used for electrically conducting the different components). The pressure-sensitive module 1230 may comprise a membrane on an MEMS die (Micro Electro Mechanical System semiconductor die). The emitter module 1220 may be arranged above a hole or window through the carrier substrate 1210 in order to emit light pulses 1222,1224 to the opposite side of the carrier substrate 1210. For example, the hole or window may be an infrared (IR) window implemented by a hole or material with low infrared absorption (e.g. silicon), but can as well be a hole, if the emitter module 1220 (IR chip) assembly may ensure an acoustically sealed back volume, for example.

The metal pads on the chips (the infrared emitter and the analyzing module) may be optionally protected by a casting compound 1460 (e.g. epoxy), if exposed corrosive metal is involved (e.g. aluminum) for example.

The analyzing module 1440 is laterally arranged between the pressure-sensitive module 1230 and the emitter module 1220 on the same side of the carrier substrate 1210. The pressure-sensitive module 1230 is connected to the analyzing module 1440 and is configured to provide the sensor signal 1232 (e.g. through a bound wire) to the analyzing module 1440. Further, the emitter module 1220 may be optionally connected to the analyzing module 1440 so that the analyzing module 1440 can trigger the emission of the light pulses by the emitter module 1220.

The emitter module 1220, the pressure-sensitive module 1230 and the analyzing module 1440 are enclosed at the surface of the carrier substrate 110 by a cap, a lid or a housing 1450. In other words, the lid 1450 covers the pressure-sensitive module 1230 (MEMS) and the analyzing module 1440 (ASIC). Optionally also the emitter module 1220 is covered delivering higher or larger back volume 1404 as shown in FIG. 14. The lid 1450 may be electrically-conductive (e.g. metal or metallized part or metal-filled polymer) and electrically connected to a ground contact to provide a shielding function. An electrical ground contact 1412 of the shielding lid 1450 to the substrate can be implemented on the carrier substrate 1210 (e.g. solder or conductive adhesive). If the lid 1450 provides the back volume (of the membrane of the pressure-sensitive module as shown in FIG. 14), the lid 1450 may be acoustically sealed to the substrate (e.g. to avoid an excitation of the backside volume by the acoustic wave caused by the emitted light pulses).

The carrier substrate 1210 may comprise one or more electrical contacts 1414 (e.g. solder ball or flat metallization or a bent metal part or through-hole contact or pin) in order to provide a connectability to other electronic devices.

The volume 1402 intended to be filled with the gas to be analyzed is arranged at an opposite of the carrier substrate 1210 with respect to the emitter module 1220, the pressure-sensitive module 1230 and the analyzing module 1440. The volume 1402 intended to be filled by the gas to be analyzed is enclosed by a housing 1403 comprising a gas inlet 1407 (e.g. for providing gas to be analyzed) and a gas outlet 1405 (e.g. for draining of gas). In this way, a gas flow can be led through the volume 1402 intended to be filled by the gas to be analyzed.

Alternatively, one hole (inlet and outlet) may be sufficient (e.g. for measuring environmental gases), which may be big enough to ensure reasonable exchange of gas in the volume 1402, for example. In other words, a cavity (volume to be filled with a gas to be analyzed) may be formed by attaching a preformed part (e.g. housing) to the substrate (carrier substrate) providing a volume with gas to be measured, for example. The volume 1402 intended to be filled by gas to be analyzed may be arranged opposite to the emitter module 1220 so that the emitter module 1220 can emit light pulses through the hole or window 1422 into the volume 1402 intended to be filled with the gas to be analyzed.

The carrier substrate 1210 comprises a hole 1406 between the pressure-sensitive module 130 and the volume 1402 intended to be filled with the gas to be analyzed at the opposite side representing an acoustic signal port so that acoustic waves caused at the opposite side of the pressure-sensitive module 1230 can reach the pressure-sensitive module 1230 through the hole 1406.

FIG. 14 shows an example for a package with components of the photoacoustic gas sensor device 1400. Further elements or modules may be implemented within such a package.

Figure 15:
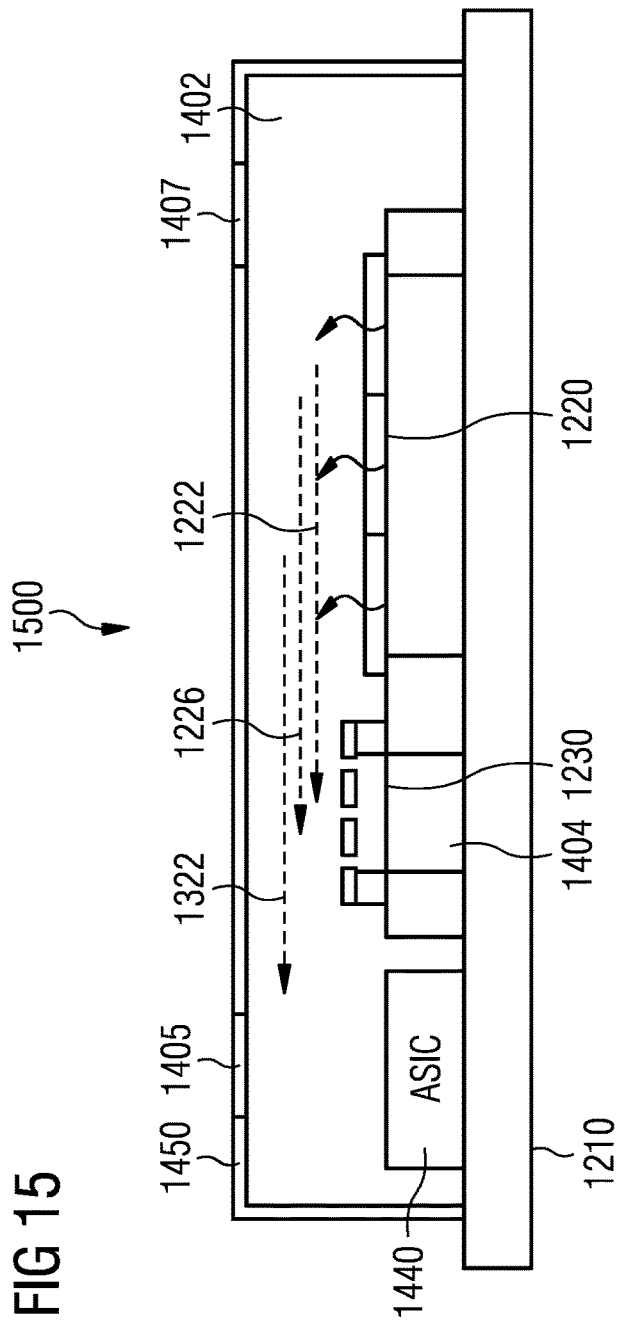

FIG. 15 shows a schematic cross section of a photoacoustic gas sensor device 1500 according to an embodiment. The implementation of the photoacoustic gas sensor device 1500 is similar to the implementation shown in FIG. 14. However, the pressure-sensitive module 1230 and the emitter module 1220 are implemented on the same semiconductor die and the emitter module 1220 comprises three emitter elements emitting different light pulses 1222, 1226, 1322 with different frequency ranges and different temporal occurrence characteristics (e.g. similar to FIG. 14). Further, the lid or cap 1450 enclosing or covering the emitter module 1220, the pressure-sensitive module 1230 and the analyzing module 1440 encloses the volume 1402 intended to be filled with the gas to be analyzed. Further, the lid 1450 comprises a first hole representing a gas inlet 1407 and a second hole representing a gas outlet 1405. More details and aspects are described in connection with FIG. 14.

FIG. 15 shows different infrared sources having narrow-band emission, for example. Each infrared source may be chopped with a special frequency that can be clearly distinguished by one microphone, for example. The emitter module 1220 may be implemented by an infrared heater (thermal emitter with three different filters on a membrane). The carrier substrate 1210 may be implemented by a printed circuit board (PCB)-based ground plate with pads for electrical contact on the lower side (opposite to the emitter module and pressure-sensitive module) for example. The acoustic effect of heating air can optionally be calibrated.

Figure 16:
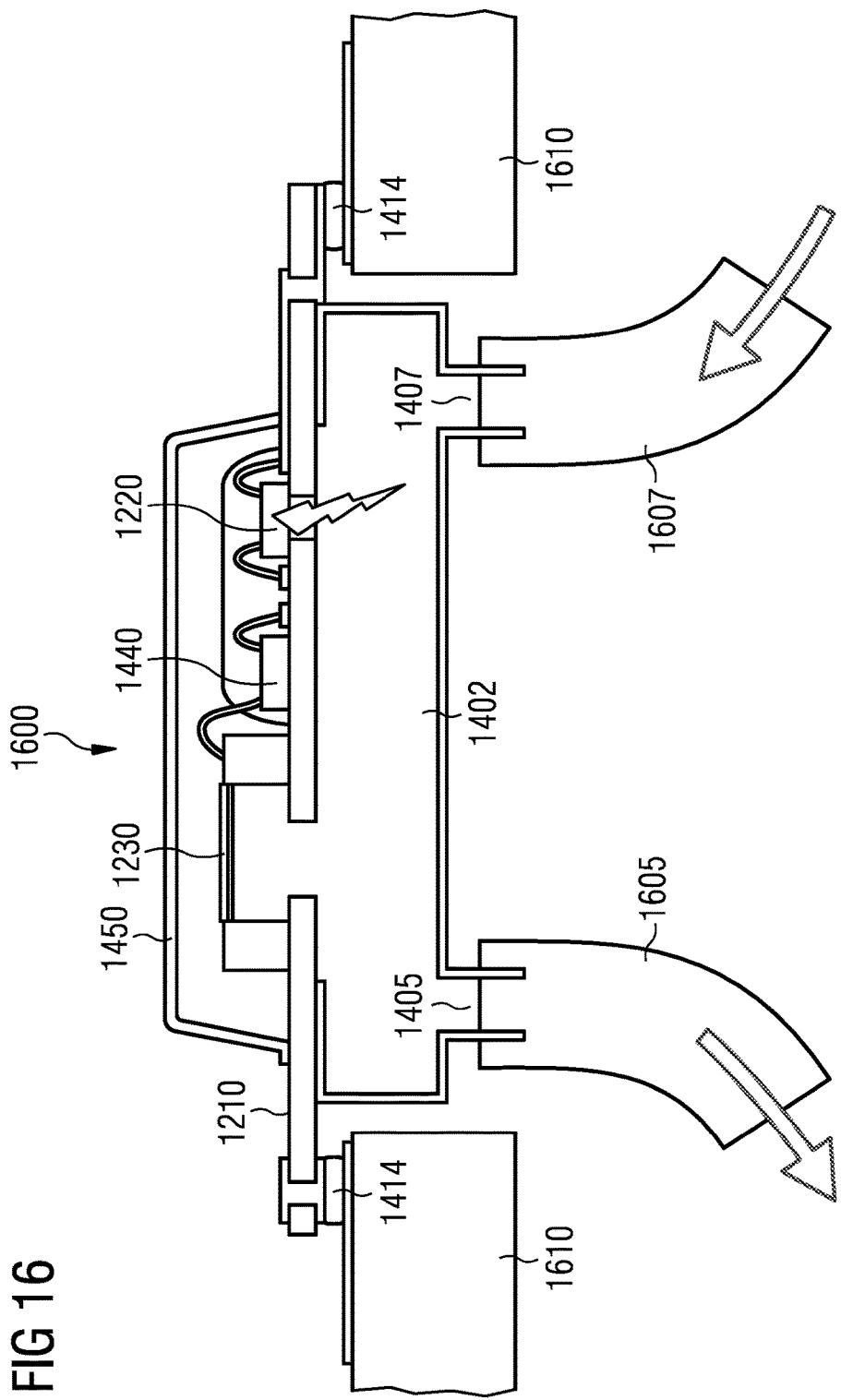

FIG. 16 shows a schematic cross-section of a photoacoustic gas sensor device 1600 according to an embodiment. The implementation of the photoacoustic gas sensor device 1600 is similar to the implementation shown in FIG. 14. Additionally, the photoacoustic gas sensor device 1600 is assembled to a printed circuit board 1610 through the electric contacts 1414 (e.g. by soldering) and a first hose 1607 is connected to the gas inlet 1407 for providing gas to be analyzed and a second hose 1605 is connected to the gas outlet 1405 in order to drain off gas. More details and aspects are described in connection with FIG. 14.

FIG. 16 shows an example for assembly of a component or the sensor to a printed circuit board (PCB) using a solder interconnect. Alternatively, interconnects can also be used. Hoses can optionally be attached to the cavity 1402 in order to guide gas from a specific location through the cavity 1402. Alternatively, the component (photoacoustic gas sensor device) can be mounted upside down (with gas inlet and outlet pointing to the top), for example.

Further variations of the orientation of the emitter module (e.g. IR emitter) may be possible. The following Figures show more possibilities and concepts for positioning at least an infrared emitter (e.g. drawn as a complete component implemented by a wire-bonded chip or a ball grid array chip, for example). The interconnection of the package terminals to the IR emitter can for instance be done by using a flex substrate or a combination between flex and rigid substrate. The position and direction of the IR beam can impact the sensor signal (e.g. the absorption-induced pressure pulse), for example.

Figure 17:
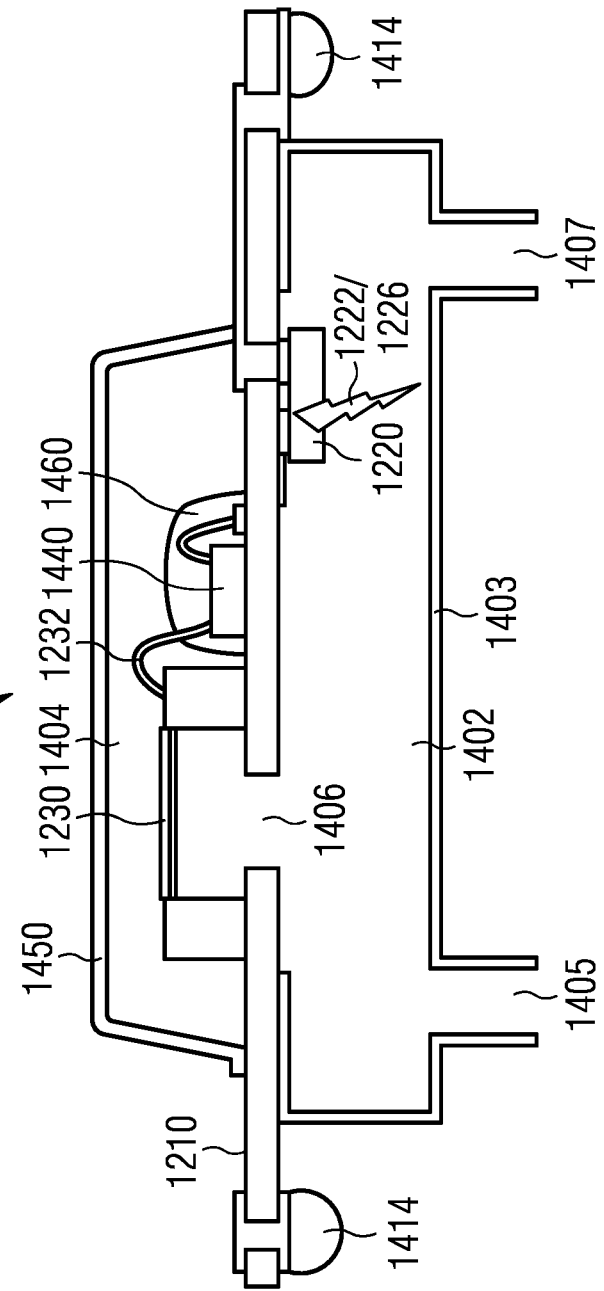

FIG. 17 shows a schematic cross-section of a photoacoustic gas sensor device 1700 according to an embodiment. The implementation of the photoacoustic gas sensor device 1700 is similar to the implementation shown in FIG. 14. However, the emitter module 1220 is arranged at a side of the carrier substrate 1210 opposite to the pressure-sensitive module 1230 and the analyzing module 1440. Further, the emitter module 120 is arranged within the volume 104 intended to be filled with the gas to be analyzed. More details and aspects are explained in connection with FIG. 14.

Figure 18:
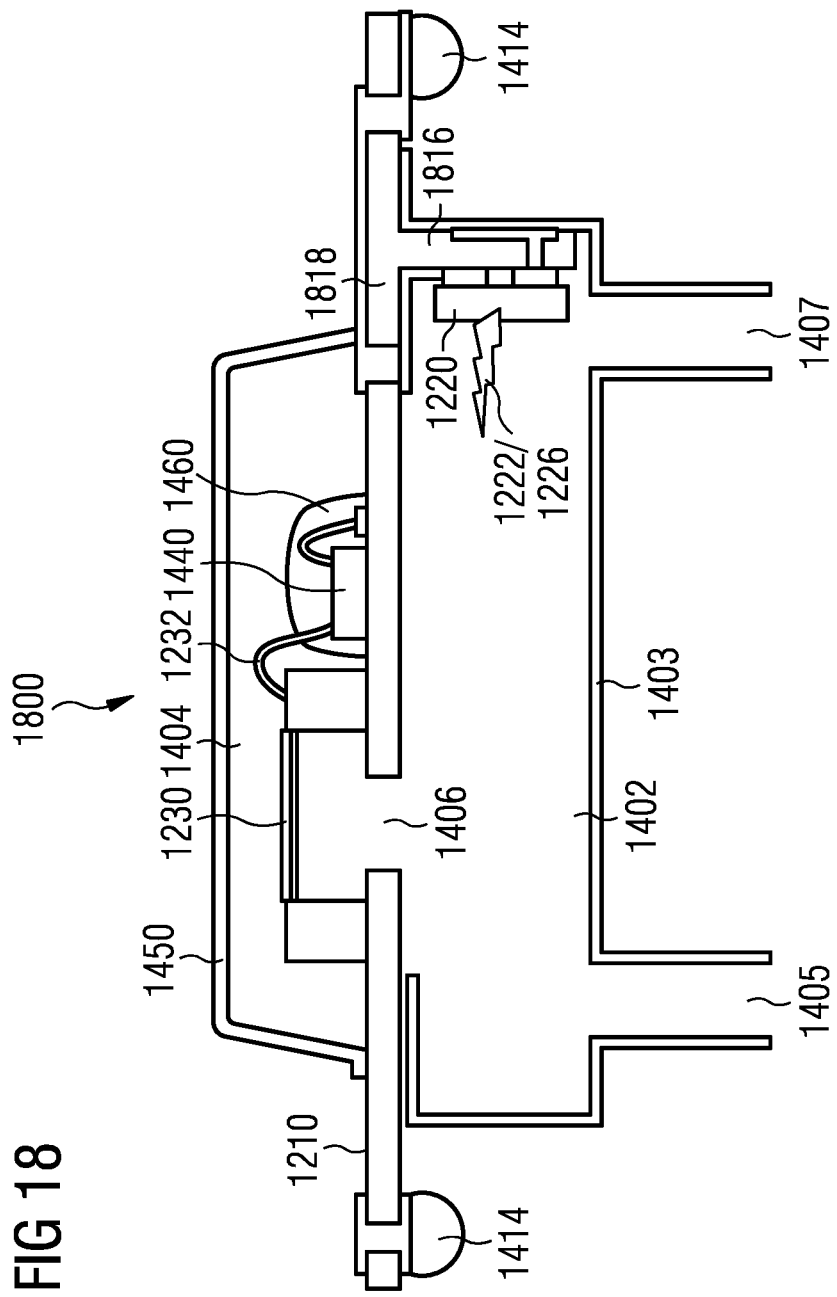

FIG. 18 shows a schematic cross-section of a photoacoustic gas sensor device 1800 according to an embodiment. The implementation of the photoacoustic gas sensor device 1800 is similar to the implementation shown in FIGS. 14 and 17. However, the carrier substrate 1210 deviates from the basically flat geometry and comprises at least an L-shaped geometry (or a T-shaped geometry). The emitter module is arranged at a first leg 1816 (e.g. the short leg) of the L-shaped geometry of the carrier substrate 1210 within the volume 1402 intended to be filled with the gas to be analyzed. Further, the pressure-sensitive module 1230 and the analyzing module 1440 are arranged at the second leg 1818 (e.g. the long leg) of the L-shaped geometry of the carrier substrate 1210. In this way, the emitter module 1220 can be arranged so that the emitted light pulses 1220 are directed in the direction of the volume 1402 intended to be filled with the gas to be analyzed. More details and aspects are described in connection with FIGS. 14 and 17.

FIG. 19 shows a schematic cross-section of a photoacoustic gas sensor device 1900 according to an embodiment. The implementation of the photoacoustic gas sensor device 1900 is similar to the implementation shown in FIGS. 14, 17 and 18. However, the carrier substrate 1210 comprises an at least U-shaped geometry (e.g. in this example a U-shape with unequally long legs and an extension of the longer leg). In other words, the carrier substrate 1210 comprises two parallel portions (legs of the U-shape) connected by a portion arranged orthogonal to the two parallel portions (bottom of the U-shape). The emitter module 1220 is arranged at the first leg 1916 of the U-shaped geometry of the carrier substrate 1210 and the pressure-sensitive module 1230 and the analyzing module 1440 are arranged at a second leg 1918 of the U-shaped geometry of the carrier substrate 1210. The emitter module 1220 is located on a side of the first leg 1816 facing the second leg 1818. The pressure-sensitive module 1230 and the analyzing module 1440 are arranged on a side of the second leg 1818 opposite to the first leg 1816. The gap between the first leg 1816 and the second leg 1818 is used for the volume 1402 intended to be filled with the gas to be analyzed. More details and aspects are described in connection with FIGS. 14, 17 and 18.

Basically, it would also be possible to not even use a gas cavity or a housing enclosing the volume intended to be filled with the gas to be analyzed, which may reduce the costs. However, reflective cavity walls or housing walls may help to create a good signal or a higher signal amplitude.

FIG. 20 shows a schematic cross-section of a photoacoustic gas sensor device 2000 according to an embodiment. The implementation of the photoacoustic gas sensor device 2000 is similar to the implementation shown in FIG. 18. However, the housing of the volume intended to be filled with a gas to be analyzed is removed. In other words, the volume to be filled with the gas to be analyzed is an open volume surrounding the emitter module 1220 as shown in FIG. 20. More details and aspects are described in connection with FIG. 18.

FIG. 21 shows a schematic cross-section of a photoacoustic gas sensor device 2100 according to an embodiment. The implementation of the photoacoustic gas sensor device 2100 is similar to the implementation shown in FIG. 14. In comparison to the example shown in FIGS. 14 to 20, the volume 104 intended to be filled with the gas to be analyzed is arranged on the same side of the carrier substrate as the emitter module 1220 and the pressure sensitive module 1230. More details and aspects are described in connection with FIGS. 12 to 14, for example.

FIG. 21 shows a version with top access to the microphone or an example for a sensor with a top acoustic port. The cross-section demonstrates a version similar to FIG. 14 but others (e.g. multiple microphones, multiple reference volumes, multiple IR-images) are possible corresponding to the embodiments shown by other Figures, for example. In the implementation shown in FIG. 21, the back volume 2104 may be given by the etched volume of the MEMS die (Micro Electro Mechanical System die representing the pressure-sensitive module). Low back volumes may result in lower signal-to-noise ratios, but may be sufficient for a large variety of applications, for example.

Some examples relate to a mobile device (e.g. cellphone, smartphone, tablet or laptop) comprising a photoacoustic gas sensor device according to the described concept or one or more embodiments described above.

Some embodiments relate to a photoacoustic sensor system or a package concept for photoacoustic gas sensors. Multiple gases can be sensed in one sensor module. Instead of using different sensors (each equipped with IR-source and microphone), the system can share either the infrared (IR-source) or the microphone to end up with lower component count, for example.

The photoacoustic sensor principle can be applied for $CO_2$ sensing, for example. The sensor may consist of a chopped thermal IR-source and a microphone. Due to the absorption of IR-light bipolar molecules generate a vibration with the frequency of the chopping that can be detected, for example. In some configurations, a reference cell can be used as positive filter, for example. An aspect of the proposed concept is the assembly of a multiple gas acoustic sensor module with reduced component count, for example.

A large variety of gases or components of gases may be detected based on the described concept. For example, $CO_2$ (carbon dioxide) can be detected in order to determine an indoor air quality or air conditioning, ethanol (vapor) for enabling a legislatively-ruled alcohol control or methane for improving the security of heating systems, indoor cooking or gas alert, for example. If a sensor module is small and cheap enough to be integrated in a handheld device (e.g. smartphones) such sensors could be implemented in huge numbers, for example.

The infrared absorption is well understood to distinguish the three components ($CO_2$, ethanol and methane). In the case of the three components (e.g. 4.3 μm for $CO_2$, 3.6 μm/9.6 μm for ethanol; 3.3 μm/7.7 μm for methane) the close spacing of ethanol absorption at 3.6 μm and the methane absorption at 3.3 μm can result in crosstalk of signal. Therefore, a mixture infrared source with 4.3 μm, 7.7 μm and 9.7 μm may be implemented, for example.

In other words, instead of multiplying gas sensors for multiple gas detection, additional selectivity in IR-radiation or chopping frequency can help in reducing the system component count.

The proposed concept provides an easily manufacturable sensor implementation comprising at least the components silicon microphone (pressure-sensitive module), IR-emitter (emitter module), logic integrated circuit (analyzing module, also called ASIC) and optionally further modules, for example.

A photoacoustic gas sensor device according to the described concept may comprise a microphone, at least one infrared emitter and at least one ASIC (analyzing module). Examples are shown in FIG. 2 or 14.

The microphone chip may be assembled so that the acoustic pressure impulse (acoustic wave) hits the membrane and the backside volume behind enables the formation of a corresponding acoustic signal. This, as well as the combination of the MEMS-chip with the ASIC may be done analog to an assembly of a silicon microphone housing, for example. The same may be valid for forming a backside volume by a cap assembly. Various substrates used in the semiconductor technology may be used for the carrier substrate (e.g. organic substrate analog to a printed port, a ceramic substrate or a metal grid or lead frame).

Additionally, an IR-emitter is integrated, which is oriented or arranged so that emitted light crosses the gas volume to be analyzed. In an implementation, the emitted light does not hit the backside volume, for example. Otherwise, pulses would be generated also there, which may lead to an acoustic signal distinction or to a degradation of the signals. The gas volume may be a defined volume enclosed by a cavity, which however enables a gas exchange with the environment (e.g. by a simple hole or a defined gas inlet and outlet opening). The overall system may comprise external connections (e.g. bent legs, pins, flat solderable areas or a soldering depot), which enables an electric conducting (e.g. to a circuit board). Some aspects relate to a selective gas detection.

Photoacoustic gas sensor devices according to the described concept may implement a cost-efficient package concept for a photoacoustic gas sensor, an integration of an infrared emitter into a silicon microphone package or housing and/or an easy assembly (e.g. by using a pick-and-place placement machine), by implementation as a surface-mounted device (SMD).

According to an aspect, a photoacoustic gas sensor can be implemented as a system-in-package (SIP) or as a surface-mounted device. The system-in-package may contain at least a silicon microphone chip, an ASIC for signal conditioning and an infrared emitter, for example.

Optionally, the system may comprise further electrical components (e.g. a circuitry for generating a modulation frequency for the infrared emitter).

FIG. 22 shows a flowchart of a method 2200 for analyzing gas according to an embodiment. The method 2200 comprises emitting 2210 light pulses by an emitter module arranged on a carrier substrate. The emitted light pulses reach a reference gas volume after crossing a volume intended to be filled with the gas to be analyzed. Further, the reference gas volume is separated from the volume intended to be filled with the gas to be analyzed. Further, the method 2200 comprises generating 2220 a sensor signal by a pressure-sensitive module arranged on the carrier substrate within the reference gas volume. The sensor signal indicates information on an acoustic wave caused by the emitted light pulses interacting with a reference gas within the reference gas volume.

Due to the placement of the emitter module so that the light pulses provided by the emitter module pass the volume intended to be filled with the gas to be analyzed before entering the reference gas volume, only the not absorbed portion of the light pulses reaches the reference gas volume and causes an acoustic wave. By implementing the emitter module and the pressure-sensitive module on a common carrier substrate in combination with a placement of the pressure-sensitive module within a reference gas volume, a gas can be analyzed with regard to one or more components contained by the reference gas with high accuracy and low effort.

The method 2200 may comprise one or more additional acts corresponding to one or more aspects mentioned in connection with the described concept or one or more embodiments described above.

FIG. 23 shows a flowchart of a method 2300 according to an embodiment. The method 2300 comprises emitting 2310 first light pulses by an emitter module arranged on a carrier substrate within a first frequency range and with a first temporal occurrence characteristic. Further, the method 2300 comprises emitting 2320 second light pulses by the emitter module within a second frequency range and with a second temporal occurrence characteristic. Additionally, the method 2300 comprises generating 2330 a sensor signal by a pressure-sensitive module arranged on the carrier substrate. The sensor signal indicates information on first acoustic waves caused by the first light pulses emitted by the emitter module interacting with the gas to be analyzed and second acoustic waves caused by the second light pulses emitted by the emitter module interacting with the gas to be analyzed.

By implementing an emitter module capable of emitting light pulses within a first frequency range and light pulses within a second frequency range, different components of a gas can be activated or excited in order to cause acoustic waves. The acoustic waves caused by the different light pulses can be differentiated by the pressure-sensitive module due to the different temporal occurrence characteristic of the first light pulses and the second light pulses. By implementing the emitter module and the pressure sensitive module on a common carrier substrate, various components of a gas can be analyzed simultaneously with low effort.

The method 2300 may comprise one or more additional optional acts corresponding to one or more aspects mentioned in connection with the proposed concept or one or more embodiments described above.

Embodiments may further provide a computer program having a program code for performing one of the above methods, when the computer program is executed on a computer or processor. A person of skill in the art would readily recognize that steps of various above-described methods may be performed by programmed computers. Herein, some embodiments are also intended to cover program storage devices, e.g., digital data storage media, which are machine or computer readable and encode machine-executable or computer-executable programs of instructions, wherein the instructions perform some or all of the acts of the above-described methods. The program storage devices may be, e.g., digital memories, magnetic storage media such as magnetic disks and magnetic tapes, hard drives, or optically readable digital data storage media. The embodiments are also intended to cover computers programmed to perform the acts of the above-described methods or (field) programmable logic arrays ((F)PLAs) or (field) programmable gate arrays ((F)PGAs), programmed to perform the acts of the above-described methods.

The description and drawings merely illustrate the principles of the disclosure. It will thus be appreciated that those skilled in the art will be able to devise various arrangements that, although not explicitly described or shown herein, embody the principles of the disclosure and are included within its spirit and scope. Furthermore, all examples recited herein are principally intended expressly to be only for pedagogical purposes to aid the reader in understanding the principles of the disclosure and the concepts contributed by the inventor(s) to furthering the art, and are to be construed as being without limitation to such specifically recited examples and conditions. Moreover, all statements herein reciting principles, aspects, and embodiments of the disclosure, as well as specific examples thereof, are intended to encompass equivalents thereof.

Functional blocks denoted as "means for . . . " (performing a certain function) shall be understood as functional blocks comprising circuitry that is configured to perform a certain function, respectively. Hence, a "means for s.th." may as well be understood as a "means configured to or suited for s.th.". A means configured to perform a certain function does, hence, not imply that such means necessarily is performing the function (at a given time instant).

Functions of various elements shown in the figures, including any functional blocks labeled as "means", "means for providing a sensor signal", "means for generating a transmit signal.", etc., may be provided through the use of dedicated hardware, such as "a signal provider", "a signal processing unit", "a processor", "a controller", etc. as well as hardware capable of executing software in association with appropriate software. Moreover, any entity described herein as "means", may correspond to or be implemented as "one or more modules", "one or more devices", "one or more units", etc. When provided by a processor, the functions may be provided by a single dedicated processor, by a single shared processor, or by a plurality of individual processors, some of which may be shared. Moreover, explicit use of the term "processor" or "controller" should not be construed to refer exclusively to hardware capable of executing software, and may implicitly include, without limitation, digital signal processor (DSP) hardware, network processor, application specific integrated circuit (ASIC), field programmable gate array (FPGA), read only memory (ROM) for storing software, random access memory (RAM), and non-volatile storage. Other hardware, conventional and/or custom, may also be included.

It should be appreciated by those skilled in the art that any block diagrams herein represent conceptual views of illustrative circuitry embodying the principles of the disclosure. Similarly, it will be appreciated that any flow charts, flow diagrams, state transition diagrams, pseudo code, and the like represent various processes which may be substantially represented in computer readable medium and so executed by a computer or processor, whether or not such computer or processor is explicitly shown.

Furthermore, the following claims are hereby incorporated into the Detailed Description, where each claim may stand on its own as a separate embodiment. While each claim may stand on its own as a separate embodiment, it is to be noted that—although a dependent claim may refer in the claims to a specific combination with one or more other claims—other embodiments may also include a combination of the dependent claim with the subject matter of each other dependent or independent claim. Such combinations are proposed herein unless it is stated that a specific combination is not intended. Furthermore, it is intended to include also features of a claim to any other independent claim even if this claim is not directly made dependent to the independent claim.

It is further to be noted that methods disclosed in the specification or in the claims may be implemented by a device having means for performing each of the respective acts of these methods.

Further, it is to be understood that the disclosure of multiple acts or functions disclosed in the specification or claims may not be construed as to be within the specific order. Therefore, the disclosure of multiple acts or functions will not limit these to a particular order unless such acts or functions are not interchangeable for technical reasons. Furthermore, in some embodiments a single act may include or may be broken into multiple sub acts. Such sub acts may be included and part of the disclosure of this single act unless explicitly excluded.

What is claimed is:

1. A photoacoustic gas sensor, comprising:
    an emitter arranged on a carrier substrate and configured to emit light pulses; and
    a semiconductor microphone arranged to have a front side facing the emitter, and configured to generate a sensor signal indicating information on an acoustic wave caused by light pulses emitted by the emitter toward the front-side of the semiconductor microphone,
    wherein the semiconductor microphone is installed in a reference gas volume filled with reference gas, a backside of the semiconductor microphone facing away from the emitter is exposed to the reference gas, and the reference gas volume is separated from a volume intended to be filled with gas to be analyzed.

2. The photoacoustic gas sensor according to claim 1, comprising an analyzer configured to determine information on the gas to be analyzed based on the sensor signal.

3. The photoacoustic gas sensor according to claim 2, wherein the analyzer is arranged on the carrier substrate and implemented on a semiconductor die different from a semiconductor die comprising the semiconductor microphone.

4. The photoacoustic gas sensor according to claim 1, wherein the semiconductor microphone comprises at least a membrane configured to be moved by the acoustic wave caused by light pulses emitted by the emitter.

5. The photoacoustic gas sensor device according to claim 1, wherein the emitter is installed in the analyzing gas volume or on the wall for forming the analyzing gas volume so that light emitted by the emitter reaches the reference gas volume after crossing the analyzing gas volume.

6. The photoacoustic gas sensor according to claim 5, wherein the reference gas volume comprises a first reference gas volume and a second reference gas volume.

7. The photoacoustic gas sensor according to claim 6, wherein the emitter is arranged so that light pulses emitted by the emitter reach the second reference gas volume after crossing the analyzing gas volume and after crossing the first reference gas volume.

8. The photoacoustic gas sensor according to claim 6, comprising a second semiconductor microphone arranged on the carrier substrate within the second reference gas volume.

9. The photoacoustic gas sensor according to claim 6, comprising a second emitter arranged on the carrier substrate and configured to emit light pulses, wherein the second emitter is arranged so that light pulses emitted by the second emitter reach the second reference gas volume after crossing the analyzing gas volume.

10. The photoacoustic gas sensor according to claim 1, wherein the emitter is configured to emit infrared light pulses.

11. The photoacoustic gas sensor according to claim 1, wherein the carrier substrate comprises a basically flat geometry or comprises at least a part with a cross section comprising a U-shaped geometry or an L-shaped geometry.

12. The photoacoustic gas sensor according to claim 11, wherein the emitter is arranged at a first leg of the L-shaped or U-shaped geometry of the carrier substrate and the semiconductor microphone is arranged at a second leg of the L-shaped or U-shaped geometry of the carrier substrate.

13. The photoacoustic gas sensor according to claim 1, wherein the emitter is configured to emit first light pulses within a first frequency range and with a first temporal occurrence characteristic and second light pulses within a second frequency range and with a second temporal occurrence characteristic, wherein the semiconductor microphone is configured to generate the sensor signal indicating information on first acoustic waves caused by the first light pulses emitted by the emitter interacting with a reference gas and second acoustic waves caused by the second light pulses emitted by the emitter interacting with a reference gas.

14. A photoacoustic gas sensor for analyzing gas comprising:
an emitter arranged on a carrier substrate and configured to emit first light pulses within a first narrow-band light frequency range and with a first temporal occurrence characteristic and second light pulses within a second narrow-band light frequency range and with a second temporal occurrence characteristic simultaneously; and
a semiconductor microphone arranged on the carrier substrate, wherein the semiconductor microphone is configured to generate a sensor signal indicating information on first acoustic waves caused by the first light pulses emitted by the emitter interacting with a gas to be analyzed and second acoustic waves caused by the second light pulses emitted by the emitter interacting with the gas to be analyzed,
wherein the semiconductor microphone is installed in a reference gas volume filled with reference gas, and the reference gas volume is separated from a volume intended to be filled with gas to be analyzed.

15. The photoacoustic gas sensor according to claim 14, wherein the emitter is configured to emit the first light pulses with a time distance of less than 20 ms representing the first temporal occurrence characteristic and the second light pulses with a time distance of more than 20 ms representing the second temporal occurrence characteristic.

16. A photoacoustic gas sensor for analyzing gas comprising:
an emitter arranged on a carrier substrate and configured to emit light pulses; and
a pressure sensor arranged on the carrier substrate within a reference gas volume, wherein the reference gas volume is separated from a volume intended to be filled with a gas to be analyzed, wherein the pressure sensor is configured to generate a sensor signal indicating information on an acoustic wave caused by light pulses emitted by the emitter module interacting with a reference gas within the reference gas volume, wherein the reference gas comprises a first reference gas and a second reference gas,
wherein the emitter module is arranged so that light pulses emitted by the emitter module reach the reference gas volume after crossing the volume intended to be filled with the gas to be analyzed,
wherein the emitter module is installed in the volume intended to be filled with the gas to be analyzed or on a wall for forming the volume intended to be filled with the gas to be analyzed, or in the reference gas volume or on a wall for forming the reference gas volume.

17. The photoacoustic gas sensor according to claim 16, comprising an analyzing module configured to determine information on the gas to be analyzed based on the sensor signal, wherein the analyzing module is arranged on the carrier substrate and implemented on a semiconductor die different from a semiconductor die comprising the pressure sensor.

* * * * *